United States Patent
Zembower et al.

(10) Patent No.: US 6,605,596 B2
(45) Date of Patent: Aug. 12, 2003

(54) INDOLOCARBAZOLE ANTICANCER AGENTS AND METHODS OF USING THEM

(75) Inventors: David E. Zembower, LaGrange, IL (US); Yongping Xie, San Diego, CA (US); Yasheen Zhou, Grayslake, IL (US)

(73) Assignee: Advanced Life Sciences, Inc., Woodridge, IL (US)

( * ) Notice: Subject to any disclaimer, the term of this patent is extended or adjusted under 35 U.S.C. 154(b) by 0 days.

(21) Appl. No.: 10/057,260

(22) Filed: Oct. 29, 2001

(65) Prior Publication Data

US 2003/0087842 A1 May 8, 2003

Related U.S. Application Data

(60) Provisional application No. 60/244,469, filed on Oct. 31, 2000.

(51) Int. Cl.$^7$ .......................... A61K 31/70; C07H 19/22

(52) U.S. Cl. .......................... 514/43; 514/25; 536/17.4; 536/17.7; 536/18.7

(58) Field of Search ..................... 514/25, 43; 536/17.7, 536/18.7, 17.4

(56) References Cited

U.S. PATENT DOCUMENTS

| | | |
|---|---|---|
| 5,106,742 A | 4/1992 | Wall et al. |
| 5,401,747 A | 3/1995 | Wall et al. |
| 5,437,996 A | 8/1995 | Kojiri et al. |
| 5,559,235 A | 9/1996 | Luzzio et al. |
| 5,589,365 A | 12/1996 | Kojiri et al. |
| 5,591,842 A | 1/1997 | Kojiri et al. |
| 5,643,760 A | 7/1997 | Kojiri et al. |
| 5,668,271 A | 9/1997 | Kojiri et al. |
| 5,804,564 A | 9/1998 | Kojiri et al. |
| 5,859,261 A | 1/1999 | Faul et al. |
| 5,883,114 A | 3/1999 | Kleinschroth |
| 5,922,860 A | 7/1999 | Kojiri et al. |

FOREIGN PATENT DOCUMENTS

| | | |
|---|---|---|
| WO | WO 96/04293 | 2/1996 |
| WO | WO 97/09339 | 3/1997 |

OTHER PUBLICATIONS

Ohkubo, et al., "Synthesis and Biological Activities of NB–506 Analogues: Effects of the Positions of two Hydroxyl Groups at the Indole Rings," *Bioorg. Med. Chem. Lett. 9*, 1999, pp. 3307–3312.

Arakawa, et al, "Novel Indolocarbazole Compound 6–N–Formylamino–12,13–dihydro–1, 11–dihydroxy–13–(β–D–glucopyranosyl)–5–H–indolo[2,3–α]pyrrolo–[3,4–c] carbazole–5,7 (6H)–dione (NB–506): It's Potent Antitumor Activities in Mice", *Cancer Research.*, vol. 55, p. 1316–1320, 1995.

Arakawa, et al., "ED–110, a Novel Indolcarbazole, Prevents the Growth of Experimental Tumors in Mice", *Japan. Journal Cancer Res.*, 84, p. 574–581, May 1993.

Batcho, et al., "Indoles from 2–Methylinitorbenzenes by Condensation with formamide Acetals Followed by Reduction: 4–Benzyloxyindole", *Organic Syntheses. Collective Volumes III*, p. 34–41, 1990.

Champoux, "Mechanism of Catalysis by Eukaryotic DNA Topoisomerase I", *Adv. Pharmacol.*, 29A, p. 71–82, 1994.

Kaneko, et al., "Two Synthetic Approaches to Rebeccamycin", *Tetrahedron Letters*, vol. 16, No. 34, p. 4015–4018, 1985.

Ohkubo, et al., "Synthesis of Dissymmetric Indolocarbazole Glycosides Using the Mitsunobu Reaction at the Glycosylation Step", *Tetrahedron*, vol. 53, No. 17, p. 5937–5950, 1997.

(List continued on next page.)

*Primary Examiner*—Elli Peselev
(74) *Attorney, Agent, or Firm*—McDonnell Boehnen Hulbert & Berghoff

(57) ABSTRACT

The present invention relates to anti-tumor compounds, compositions and methods. In particular, the invention relates to indolocarbazole analogues of the following general formulas that inhibit topoisomerase I activity

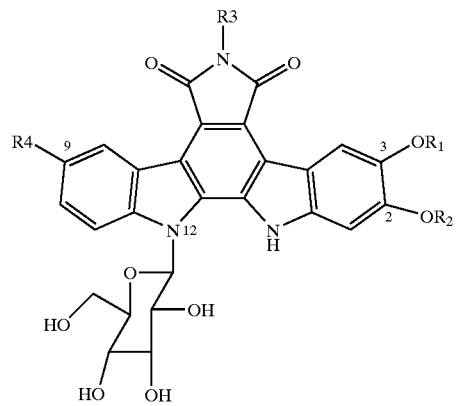

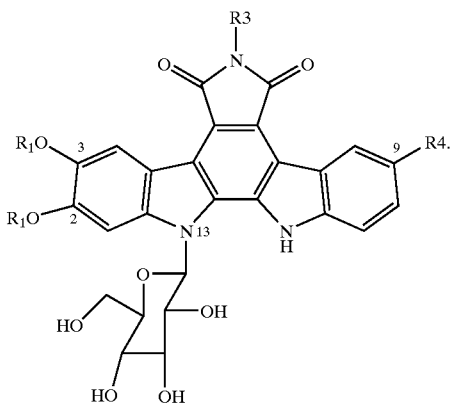

42 Claims, No Drawings

OTHER PUBLICATIONS

Pommier, et al., "Mechanisms of Topoisomerase I Inhibition by Anticancer Drugs",*Advances in Pharmacology,* vol. 29B, p. 73–92, 1994.

Redinbo, et al., "Crystal Structures of Human Topoisomerase I in Covalent and Noncovalent Complexes with DNA", *Science,* vol. 279, p. 1504–1513, 1998.

Yoshinari, et al., "Mode of Action of a New Indolocarbazole Anticancer Agent, J–107088, Targeting Topoisomerase I" *Cancer Research,* vol. 59, p. 4271–4275, 1999.

Zembower, et al., "Indolocarbazole Poisons of Human Topoisomerase I: Regiosiomeric Analogues of ED–110", *Bioorganic & Medicinal Chemistry Letters 9,* p. 145–150, 1999.

Anizon, et al., "Syntheses and Biological Activities (Topoisomerase Inhibition and Antitumor and Antimicrobial Properties) of Rebeccamycin Analogues Bearing Modified Sugar Moieties and Substituted on the Imide Nitrogen with a Methyl Group," *J. Med. Chem,* vol. 40, 1997, pp. 3456–3465.

Glossary Entry for Anomer, p. 1 of 1, http://www.vei.co.uk/TGN/glossary/entries/anomer.html.

Molecular Recognition of Carboydrates, pp. 1–6, http://www.nmr.chem.uu.nl/~abonvin/ToT/damm/index.html.

Monosaccharides Form Rings, pp. 1–2, Cabrillo College Chem 12B, Spring 1998, http://www.cabrillo.cc.ca.us./divisions/becho/ chem/hungar/exercise_3/html/12b33.html.

Nomenclature of Carbohydrates (Recommendations 1996) 2–Carb–33, pp. 1–9, http://www.chem.qmw.ac.uk/iupac/2carb/33.html.

Pereira, et al., "Structure–Activity Relationship in a Series of Substituted Indolocarbazoles: Topoisomerase I and Protein Kinase C Inhibiton and Antitumoral and Antimicrobial Properties," *J. Med. Chem.* vol. 39, 1996, pp. 4471–4477.

Preventiion of Anomer Separation, Monosaccharides and oligosaccharides, p. 1, http://www.hplc1.com/shodez/english/dc030202.htm.

Sci.chem FAQ—Part 7 of 7, http://www.fags.org/fags/sci/chem–faq/part7/preamble.html.

Stereo Oligomers and Polymers from Glycals: Oligomerisations, pp. 1–2, http://www.ch.ic.ac.uk./ectoc/echet196/papers/008/oligomers.html.

Stereochemistry of Glycosyl Transfer: Interaction with "glucose" Active site of the Enzyme, pp. 1–2, http://www.netsci–jounal.com/97v1/97005/005p30.htm.

Yamashita, et al., "Induction of Mammalian DNA Topoisomerase I Mediated DNA Cleavage by Antitumor Indolocarbazole Derivatives," *Biochemistry* 1992, vol. 31, pp. 12069–12075.

Zembower, et al., "Indolocarbazole Poisons of Human Topoisomerase I: Regioisomeric Analogues of ED–110" *Bioorganic & Medicinal Chemistry Letters 9,* 1999, pp. 145–150.

INDOLOCARBAZOLE ANTICANCER AGENTS AND METHODS OF USING THEM

This Application claims the benefit of Provisional Application Ser. No. 60/244,469 filed Oct. 31, 2000.

FIELD OF THE INVENTION

This invention relates to synthetic indolocarbazole analogues and uses thereof. More particularly, this invention relates to modifications of the core structure 12-(β-D-gluocopyranosyl)-6,7,12,13-tetrahydroindolo[2,3-a]pyrrolo[3,4-c]carbazole-5,7-dione, containing substitutions consisting of a 2,3,9-trihydroxy pattern, particularly cyclic and acyclic ethers at the 2- and 3-hydroxy positions. This invention also relates to compositions and methods of using such indolocarbazole analogues for the inhibition of topoisomerase I activity.

BACKGROUND OF THE INVENTION

Human topoisomerase I (Topo I) is an enzyme critical to the viability of cellular function that is an attractive target for the design and development of anticancer therapeutics. Currently there are two anticancer agents approved by the Food and Drug Administration for the clinical treatment of cancers: topotecan (Hycamtin) and CPT-11 (Camptosar), both of which are structural analogues of the natural product camptothecin.

Topo I is a 100 kD monomeric protein that catalyzes changes in the topological state of double-stranded DNA (dsDNA) in increments of one linking number[1]. The three-dimensional structure of human Topo I has been reported[2]. The mechanism by which Topo I acts is believed to proceed through induction of a transient single-stranded break in dsDNA via formation of a covalent protein-DNA adduct referred to as the cleavable complex, so named because these complexes are detected as DNA breaks upon treatment with denaturing agents or alkali. The cleavable complex is formed upon transesterification of a DNA phosphodiester linkage by the active site tyrosine-723 residue on human Topo 1, resulting in an ester linkage between the enzyme and the 3'-phosphoryl end of the broken DNA strand. This allows free rotation of the protein-bound 3' end of the broken DNA strand about the intact complementary DNA strand, resulting in relaxation of the duplex in increments of one linking number. Religation of the broken strand (via a second transesterification reaction) and subsequent dissociation of topoisomerase I completes the catalytic cycle.

Topoisomerase I poisons act via stabilization of the cleavable complex, mediated by formation of a ternary complex consisting of drug, topoisomerase I and DNA[3]. Agents such as camptothecin (the prototype topoisomerase I poison) do not bind to DNA directly, nor to topoisomerase I alone, but only to topoisomerase I complexed with DNA. It has been postulated that the stabilized DNA-protein-drug complex causes lethal DNA strand breaks upon collision with the advancing replication fork. It is by this mechanism that the topoisomerase I poison converts the enzyme into a DNA damaging agent, resulting in disruption of DNA replication and, eventually, cell death. This postulate is supported by the fact that camptothecin is highly phase-specific, only killing cells in S-phase.

In addition to the camptothecins, indolocarbazoles have also demonstrated potent antitumor activity via the poisoning of topoisomerase I activity[4-7], most notably ED-110[8]NB-506[9], and J-107088[10]. The indolocarbazole analogue bearing a 3,9-dihydroxy substitution pattern was found to have superior topoisomerase I poisoning capability as well as superior in vitro antitumor activity relative to the other "symmetrical" dihydroxylated regioisomers[11]. The 3,9-dihydroxy analogue also exhibited impressive in vivo antitumor activity against the DU-145 human prostate tumor line xenotransplanted into nude mice.

SUMMARY OF THE INVENTION

The present invention relates to compounds, compositions and methods for the inhibition of topoisomerase I activity.

Accordingly, one object of the invention is to provide compounds of the general formulas I and II,

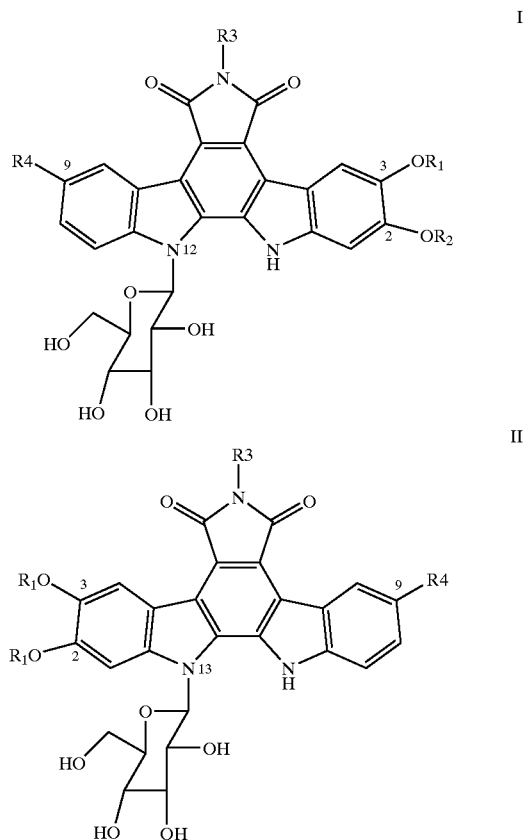

wherein $R_1$ and $R_2$ are independently H, $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl, cyclo($C_{3-6}$)alkyl, or an aryl, wherein the aryl comprises of six membered aromatic carbocycle such as phenyl or a polycyclic aromatic hydrocarbon such as naphthyl, phenanthracenyl, indanyl or a heterocycle wherein the heterocyle comprises of six membered aromatic heterocycles such as piridyl, diazinyl, pyrimidinyl, pyrrolidinyl, piperazinyl, or five membered aromatic heterocyles such as pyrrolyl, pyrazole, imidazolyl, imidazolidinyl, imidazolenyl, oxazolyl, isoxazolyl, thiazolyl, thiazolidinyl, thiazolinyl, isothiazolyl, isothiazolidinyl, isothiazolinyl, furanyl, thiophenyl or bycyclic systems such as indolyl, benzthiopheneyl, benzofuranyl, isoindolyl, isobenzothiophenyl, isobenzofuranyl; wherein the aryl or the heterocycle may each be unsubstituted or substituted with one or more of the following: $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl;

or $R_1$ and $R_2$ combine to form a ring ranging in total ring size from five ($R_1=R_2=CH_2$) to nine ($R_1=R_2=(CH_2)_5$), wherein one or more of the methylene($CH_2$) hydrogen atoms may be replaced with halogen, $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl) amino, $C_{1-8}$ alkylamino-$C_{1-8}$ alkyl, di($C_{1-6}$ alkyl) amino-$C_{1-8}$ alkyl, cyclo($C_{3-6}$)alkyl, or an aryl, wherein the aryl comprises of any six membered aromatic carbocycle such as phenyl or a polycyclic aromatic hydrocarbon such as naphthyl, phenanthracenyl, indanyl or a heterocycle wherein the heterocyle comprises of six membered aromatic heterocycles such as piridyl, diazinyl, pyrimidinyl, pyrrolidinyl, piperazinyl, or five membered aromatic heterocyles such as pyrrolyl, pyrazole, imidazolyl, imidazolidinyl, imidazolenyl, oxazolyl, isoxazolyl, thiazolyl, thiazolidinyl, thiazolinyl, isothiazolyl, isothiazolidinyl, isothiazolinyl, furanyl, thiophenyl or bycyclic systems such as indolyl, benzthiopheneyl, benzofuranyl, isoindolyl, isobenzothiophenyl, isobenzofuranyl; wherein the aryl or the heterocycle may each be unsubstituted or substituted with one or more of the following: $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl) amino-$C_{1-8}$ alkyl;

$R_3$ comprises H or $NH_2$, nitrilo ($C_{1-6}$)alkyl amine of the formula —NH-alkyl-CN, 2-pyrrolidinyl ethyl-1-amine, benzyl amine, 2-naphthyl amine, 2-benzothiazole amine, beta phenethyl amine, 1-piperazine amine, 4-(2-hydroxyethyl) piperazine-1-amine, piperidine-1-amine, aniline, 2-hydroxy butyl amine, 3-sulfolane amine, 4-methyl 2,3 dihydro isocytosine, ($C_{1-6}$)alkyl sulfonamidyl, 2-(1H-1,2,4-triazol-1yl)acetamidyl, 1,4-dimethylpiperazine-2-formamidyl, phenoxyformamidyl, gluconamidyl, manonamidyl, gulonamidyl, or aryl carbamate: of the formula —NH—CO—Ar, wherein the aryl comprises of six membered aromatic carbocycles comprising phenyl, hydroxy phenyl, dihydroxy phenyl, trihydroxy phenyl, or a polycyclic aromatic hydrocarbon such as naphthyl, phenanthracenyl, indanyl, or heterocycle carbamate of the formula —NH—CO-heterocycle: wherein the heterocyle comprises of six membered aromatic heterocycles comprising piridyl, diazinyl, pyrimidinyl, 5-methoxy pyrimidinyl, pyrrolidinyl, (1,2,4)triazine-3,5-dione-6-yl, 6-mercaptopyrimidine-4yl, or six membered non-aromatic heterocycles comprising piperazinyl, 4-methyl piperazinyl, pyranyl, or five membered aromatic heterocycles comprising pyrrolyl, 1-methyl pyrrol-2-yl, pyrazolyl, imidazolyl, imidazolidinyl, imidazolenyl, oxazolyl, isoxazolyl, thiazolyl, 2-methyl thiazol-4-yl, thiazolidinyl, thiazolinyl, isothiazolyl, isothiazolidinyl, isothiazolinyl, furan-2-yl, thiophen-2-yl, thiophen-3-yl, 3'-methoxy thiophen-3-yl, or bycyclic systems such as indolyl, benzthiopheneyl, benzofuranyl, isoindolyl, isobenzothiophenyl, isobenzofuranyl or alkyl carbamate of the formula —NH—CO-alkane, where in the alkane comprises ($C_{1-6}$)alkyl, 4-methyl piperazinyl methyl, or morpholino ($C_{1-6}$)alkyl, piperazino ($C_{1-6}$)alkyl, or nitrilo ($C_{1-6}$)acyl, or an aryl, wherein the aryl comprises of any six membered aromatic carbocycle such as phenyl or a polycyclic aromatic hydrocarbon such as naphthyl, phenanthracenyl, indanyl or a heterocycle wherein the heterocyle comprises of six membered aromatic heterocycles such as piridyl, diazinyl, pyrimidinyl, pyrrolidinyl, piperazinyl, or five membered aromatic heterocyles comprising pyrrolyl, pyrazole, imidazolyl, imidazolidinyl, imidazolenyl, oxazolyl, isoxazolyl, thiazolyl, thiazolidinyl, thiazolinyl, isothiazolyl, isothiazolidinyl, isothiazolinyl, furanyl, thiophenyl or bycyclic systems comprising indolyl, benzthiopheneyl,benzofuranyl, isoindolyl, isobenzothiophenyl, isobenzofuranyl; wherein the aryl or the heterocycle may each be unsubstituted or substituted with one or more of the following: $C_{1-6}$ alkyl, $C_{1-6}$ alkoxy, $C_{1-6}$ alkylamino, di($C_{1-6}$ alkyl)amino, $C_{1-8}$ alkylamino-$C_{1-6}$ alkyl, di($C_{1-6}$ alkyl) amino-$C_{1-8}$ alkyl;

or $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl) amino, $C_{1-8}$ alkylamino-$C_{1-8}$ alkyl, di($C_{1-6}$ alkyl) amino-$C_{1-8}$ alkyl, cyclo($C_{3-6}$)alkyl, hydroxy ($C_{1-6}$) alkyl, dihydroxy ($C_{1-6}$)alkyl, $R_4$ comprises H, $NH_2$, $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl, cyclo($C_{3-6}$)alkyl, or an aryl, wherein the aryl comprises of any six membered aromatic carbocycle such as phenyl or a polycyclic aromatic hydrocarbon such as naphthyl, phenanthracenyl, indanyl or a heterocycle wherein the heterocyle comprises of six membered aromatic heterocycles such as piridyl, diazinyl, pyrimidinyl, pyrrolidinyl, piperazinyl, or five membered aromatic heterocycles such as pyrrolyl, pyrazole, imidazolyl, imidazolidinyl, imidazolenyl, oxazolyl, isoxazolyl, thiazolyl, thiazolidinyl, thiazolinyl, isothiazolyl, isothiazolidinyl, isothiazolinyl, furanyl, thiophenyl or bycyclic systems such as indolyl, benzthiopheneyl, benzofuranyl, isoindolyl, isobenzothiophenyl, isobenzofuranyl; wherein aryl or heterocycle may each be unsubstituted or substituted with one or more of the following: $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl;

or a pharmaceutically acceptable salt thereof.

The preferred compounds are wherein $R_1$ and $R_2$ combine to form a methylenedioxy ring, $R_3$ is H, and $R_4$ is OH; or Wherein $R_1$ and $R_2$ combine to form an ethylenedioxy ring, $R_3$ is H, and $R_4$ is OH; or Wherein $R_1$ and $R_2$ combine to form an isopropylenedioxy ring, $R_3$ is H, and $R_4$ is OH; or Wherein $R_1$ and $R_2$ are both $CH_3$, $R_3$ is H, and $R_4$ is OH; or Wherein $R_1$ and $R_2$ are both H, $R_3$ is H, and $R_4$ is OH.

Another object of the invention is to provide a method of inhibiting toposisomerase I activity in a mammal comprising administering to a mammal in need of inhibition of topoisomerase I activity an effective amount of a compound of the formula I or II.

Yet another object of the invention is to provide compositions for inhibiting topoisomerase I activity in a mammal in need of inhibition of topoisomerase I activity an effective amount of at least one compound of the formulas I and II.

These and other objects of the invention will be clear in light of the detailed description below.

DETAILED DESCRIPTION OF THE INVENTION

The compounds disclosed in the present invention are useful as antitumor agents for the treatment or prevention of cancer, either alone or with a carrier. Cytotoxic agents are often employed as anticancer agents to control or eradicate tumors. Topo I poisons are useful cytotoxic agents, and two Topo I poisons related to camptothecin, Camptosar and Hycamtin (topotecan) are currently used clinically for the treatment of tumors. Indolocarbazoles are a different class of Topo I poison that represent useful agents for the treatment of tumors. In particular, Topo I-poisoning compounds disclosed in this invention were shown to be highly cytotoxic against human ovarian and prostate tumor cells.

Indolocarbazole analogues of this invention may be formulated as a solution of lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or in buffered sodium or ammonium acetate solution. Such formulation is especially suitable for parenteral administration, but may also be used for oral administration. It may be desirable to add excipients such as polyvinylpyrrolidone, gelatin, hydroxycellulose, acacia, polyethylene glycol, mannitol, sodium chloride, or sodium acetate.

Alternatively, the compounds of the present invention may be encapsulated, tableted, or incorporated into an emulsion (oil-in-water or water-in-oil) syrup for oral administration. Pharmaceutically acceptable solids or liquid carriers, which are generally known in the pharmaceutical formulary arts, may be added to enhance or stabilize the composition, or to facilitate preparation of the composition. Solid carriers include starch (corn or potato), lactose, calcium sulfate dihydrate, terra alba, croscarmellose sodium, magnesium stearate or stearic acid, talc, pectin, acacia, agar, gelatin, maltodextrins and microcrystalline cellulose, or colloidal silicon dioxide. Liquid carriers include syrup, peanut oil, olive oil, corn oil, sesame oil, saline, and water. The carrier may also include a sustained release material such as glyceryl monostearate or glyceryl distearate, alone or with a wax. The amount of solid carrier varies but, preferably, will be between about 10 mg to about 1 g per dosage unit.

The dosage ranges for administration of indolocarbazole analogues disclosed in this invention are those to produce the desired affect. The dosage will generally vary with age, body weight, extent of the disease, and contraindications, if any. The dosage will also be determined by the existence of any adverse side effects that may accompany the compounds. It is always desirable, whenever possible, to keep adverse side effects to a minimum. One skilled in the art can easily determine the appropriate dosage, scheduling, and method of administration for the exact formulation of the composition being used in order to achieve the desired effective concentration in the individual patient. However, the dosage can vary from between about 1 mg/kg/day to about 500 mg/kg/day, and preferable from between about 1 mg/kg/day to about 50 mg/kg/day.

One skilled in the art will recognize that modifications may be made in the present invention without deviating from the spirit or scope of the invention. The invention is illustrated further by the following examples, which are not to be construed as limiting the invention in spirit or scope to the specific procedures or compositions described in them.

Synthesis of Target Molecules

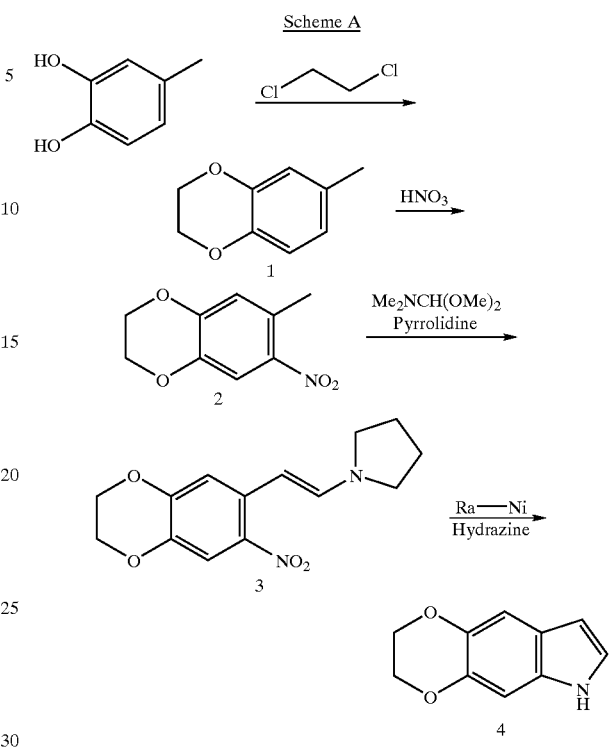

Scheme A

The required 5,6-indolodioxan and 5,6-indolodioxole precursors can be prepared starting from 4-methylcatechol, as illustrated in Scheme A for 5,6-ethylenedioxyindole (4). Protection of the ortho-dihydroxy function was achieved using 1,2-dibromoethane, dichloromethane, and acetone, respectively. Nitration using fuming nitric acid followed by indole formation using the Batcho-Leimgruber protocol[12] afforded the desired indoles.

Construction of indolocarbazole analogues can be conducted as illustrated in Scheme B for Ia. N-Benzyloxymethyl-3,4-dibromomaleimide was prepared as previously described[13]. Reaction with an appropriate indole, which had been pre-treated using an organometallic, preferably but not limited to methylmagnesium halide or lithium hexamethyldisilazide, afforded the bromoindolomaleimide intermediates represented by 5. Glucosidation at the indole nitrogen was achieved with 2,3,4,6-tetra-O-benzyl-D-glucose under Mitsunobu conditions[14] (3 equivalents each of the glucose, PPh$_3$, and diisopropylazodicarboxylate (DIAD), followed by reversed-phase purification to afford 6. Introduction of the second indole unit was conducted under conditions similar to introduction of the first indole unit, providing the bis-indolylmaleimides represented by 7. Oxidative cyclization of the bis-indolylmaleimides was achieved using either palladium(II)trifluoroacetate in DMF, or via photochemical cyclization, providing indolocarbazoles represented by 8. Others[14] reported oxidative cyclization using alternative reagents such as CuCl$_2$ and PdCl$_2$, but these failed to catalyze the reaction in our hands. Hydrogenolysis of the protective groups (palladium hydroxide, HOAc) afforded the 6-N-hydroxymethyl derivatives represented by 9, which were readily converted to the desired final products, represented by Ia, using ammonium acetate in methanol. All compounds provided spectral and analytical characteristics ($^1$H NMR, $^{13}$C NMR, MS and elemental analysis) consistent with the targeted structures.

Scheme B

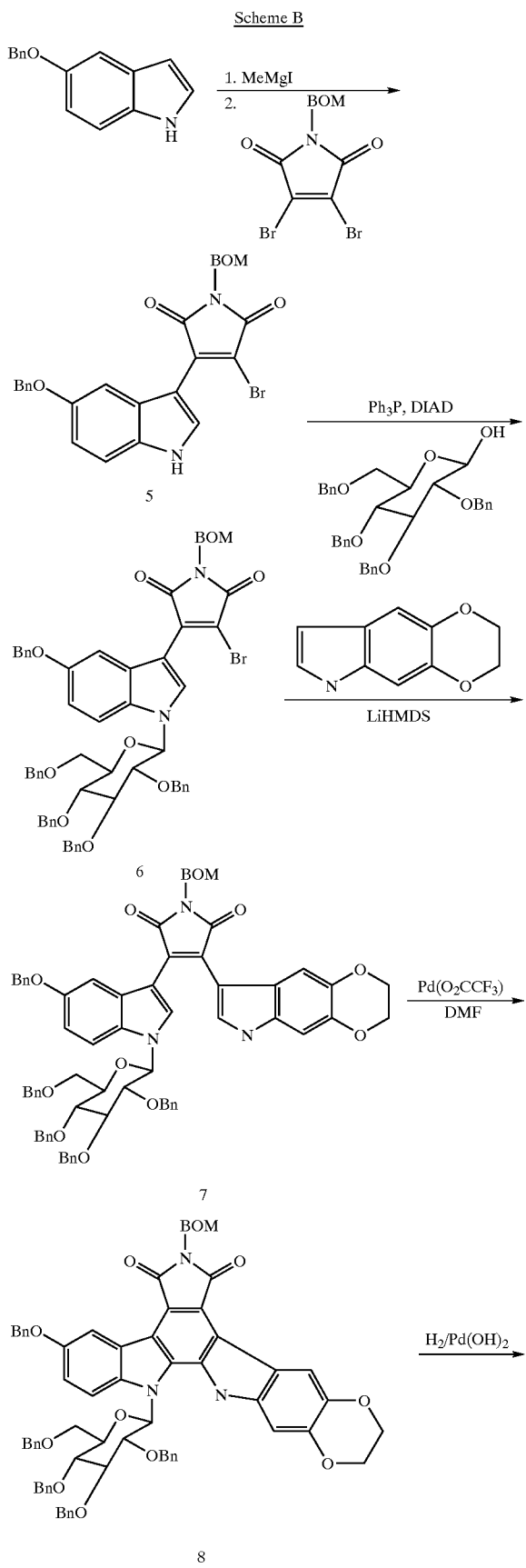

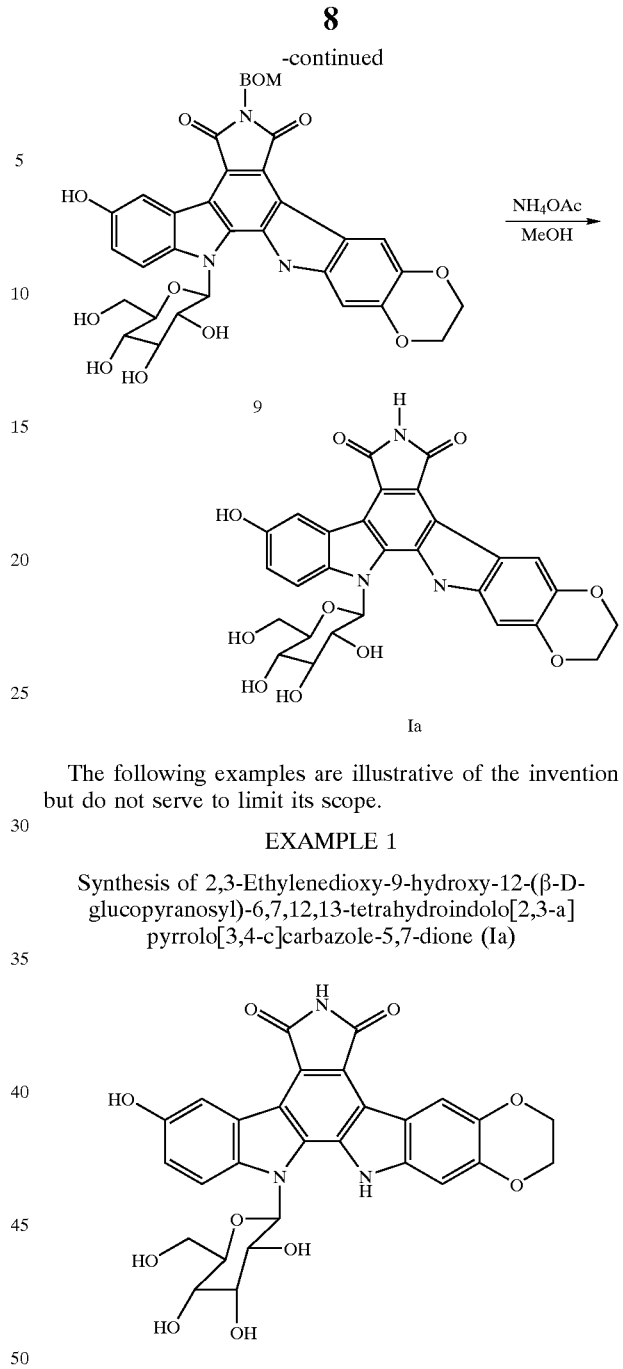

The following examples are illustrative of the invention but do not serve to limit its scope.

EXAMPLE 1

Synthesis of 2,3-Ethylenedioxy-9-hydroxy-12-(β-D-glucopyranosyl)-6,7,12,13-tetrahydroindolo[2,3-a]pyrrolo[3,4-c]carbazole-5,7-dione (Ia)

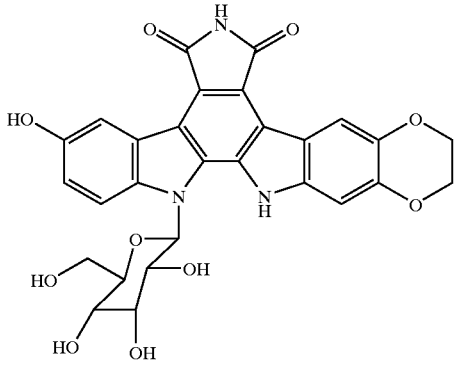

Step A: Preparation of 6-Methyl-1,4-benzodioxane (1)

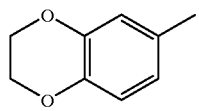

A mixture of 4-methylcatechol (33.04 g, 266.1 mmol), 1,2-dibromoethane (100 g, 532.3 mmol), $K_2CO_3$ (75.4 g, 545.5 mmol) and sodium iodide (0.2 g, 1.33 mmol) in ethylene glycol (500 mL) was heated to 130° C. under nitrogen for five hours. The solution was allowed to cool to ambient temperature and stirred overnight. After the mixture was filtered through celite, the solution was diluted with brine (800 mL) and extracted with organic solvents ($CH_2Cl_2$/hexane/EtOAc: 1:3:1,3×500 mL). The organic layer was dried over Na$_2$SO$_4$, filtered and concentrated to provide a crude oil. Flash silica gel chromatography eluting with hexane (100%) gradient to ether/hexane (8:2) afforded the title intermediate as a colorless oil 20.0 g (50%).

Step B: Preparation of 6-Methyl-7-nitro-1,4-benzodioxane (2)

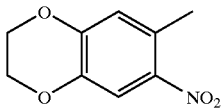

To a solution of 1 (20.0 g, 133.3 mmol) in acetic acid (135 mL) was added a solution of fuming HNO$_3$ (10 mL) in acetic acid (50 mL) dropwise over 30 minutes. The mixture was stirred at ambient temperature for 10 minutes, then poured into a beaker containing ice to give a crystalline precipitate, which was collected by vacuum filtration and washed with water to afford the product (25.8 g, 99.2 %) as an off-white solid.

Step C: Preparation of (E)-4,5-Ethylenedioxy-2-nitro-1-pyrrolidinostyrene (3)

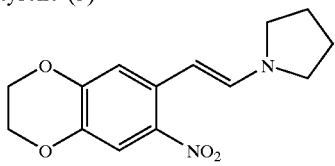

A solution of 2 (19.5 g, 100 mmol), N,N-dimethylformamide dimethyl acetal (23.63 g, 198.3 mmol) and pyrrolidine (14.1 g, 198.3 mmol) was heated to 110° C. and stirred for 24 hours under nitrogen. The reaction mixture was cooled, and 250 mL absolute methanol was added. The product crystallized as a bright red solid. Recovery by suction filtration afforded the product (24.3 g, 88.0%).

Step D: Preparation of 4,5-Ethylenedioxyindole (4)

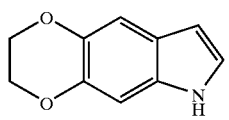

To a solution of 3 (24.0 g, 87.0 mmol) in methanol and THF (240 mL, 1:1) was added Raney nickel (2.0 mL) and hydrazine hydrate (3×3.6 mL, 348 mmol) every half hour at ambient temperature under nitrogen. Then, the solution was heated at 45° C. for two hours. The mixture was cooled to room temperature and the catalyst is removed by filtration through a bed of Celite and washed three times with methylene chloride. The filtrate was evaporated and the residue dried by evaporating with toluene (100 mL) to give a crude oil. Flash silica gel column purification eluting with hexane (100%) gradient to ethyl acetate/hexane (40/60%) afforded the title intermediate as an off-white solid (7.0 g, 46.1%).

Step E: Preparation of 2-Bromo-3-(5-benzyloxy-1H-indol-3-yl)-N-benzyloxynmethylmaleimide (5)

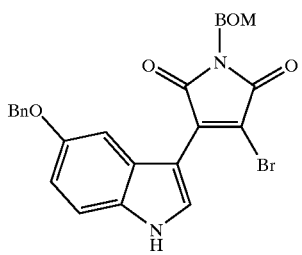

To a solution of 5-benzyloxyindole (8.93 g, 40 mmol) in benzene (150 mL) was added methylmagnesium iodide (14.7 mL, 44.0 mmol, 3 M in ether) at 0° C. The solution was stirred for one hour, and then a solution of N-benzyloxymethyl-3,4-dibromomaleimide (15.0 g, 40 mmol) in benzene (50 mL) and THF (100 mL) was added. The reaction mixture was stirred at 0° C. for 30 minutes and then warmed to room temperature and stirred for one hour. The mixture was diluted with EtOAc (350 mL) then washed with HCL (150 mL, 0.3 N), NaHCO$_3$ (200 mL) and H$_2$O (200 mL). The organic layer was dried over Na$_2$SO$_4$, filtered and concentrated. Crystallization of the crude oil with methanol afforded the title intermediate as a yellow solid (12.50 g, 66.0%).

Step F: Preparation of 2-Bromo-3-[5-benzyloxy-1-(2,3,4,5-tetra-O-benzyl-β-D-glucopyranosyl)-1H-indol-3-yl]-N-benzyloxymethylmaleimide (6)

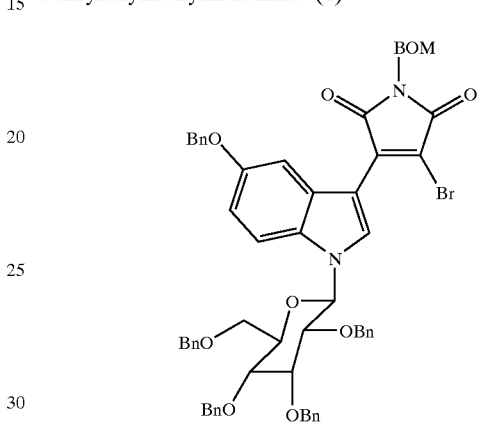

A solution of 5(15.0 g, 29.0 mmol), 2,3,4,5-tetra-O-benzyl-D-glucopyranose (47.02 g, 87.0 mmol) and triphenylphosphine (22.8 g, 87.0 mmol) in THF (800 mL) was cooled to −78° C. Diisopropylazodicarboxylate (17.14 mL, 87.0 mmol) was added dropwise, maintaining the temperature at −78° C., and then stirred for three hours. The solution was warmed to 0° C. with the aid of an ice-water bath and stirring was continued for two hours. The mixture was diluted with EtOAc (1200 mL), washed with HCl, brine, and H$_2$O. The organic layer was dried over Na$_2$SO$_4$, filtered and concentrated. The crude mixture was applied to a reversed-phase Biotage cartridge and eluted with a CH$_3$CN/H$_2$O (50/50) gradient to CH$_3$CN (100%) afforded the title intermediate as a yellow solid 22.3 g (74.0%).

Step G: Preparation of 3-(4,5-Ethylenedioxy-1H-indol-3-yl)-4-[5-benzyloxy-1-(2,3,4,5-tetra-O-benzyl-β-D-glucopyranosyl)-1H-indol-3-yl]-N-benzyloxymethyl maleimide (7)

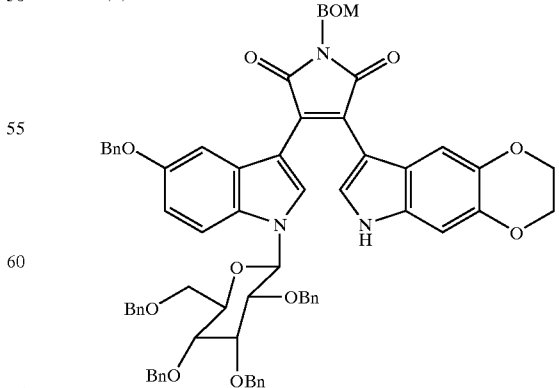

To a solution of 4 (303.2 mg, 1.73 mmol) in THF (35 mL) was added lithium hexamethyldisilazide (LiHMDS, 3.46 mL, 3.46 mmol, 1 M in THF) at 0° C., and the resulting solution stirred for 40 minutes. A solution of 6 in THF (20 mL) was added slowly to the above mixture, followed by stirring for 20 minutes at 0° C. The mixture was diluted with EtOAc (300 mL), washed with HCl (2 M), NaHCO$_3$, brine, and H$_2$O. The organic layer was dried over Na$_2$SO$_4$, filtered and concentrated to give a crude mixture. Flash silica gel chromatography eluting with a hexane (100%) gradient to EtOAc/hexane (40/60) afforded the title intermediate as a red solid 1.20 g (73.2%).

Step H: Preparation of 2,3-Ethylenedioxy-6-benzyloxymethyl-9-benzyloxy-12-(2,3,4,5-tetra-O-benzyl-β-D-glucopyranosyl)-6,7,12,13-tetrahydroindolo[2,3-a]pyrrolo[3,4-c]carbazole-5,7-dione (8)

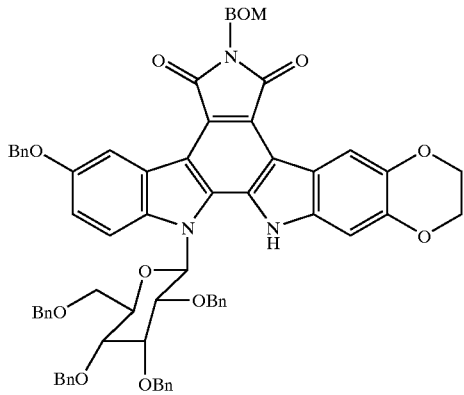

To a solution of 8 (550 mg, 0.485 mmol) in DMF (28 mL) was added palladium(II) trifluoroacetate (338.5 mg, 1.18 mmol), and stirred at 80° C. for one hour. The solution was cooled to room temperature, diluted with EtOAc (280 mL), and washed with HCl (1 M), NaHCO$_3$, brine (150 mL) and H$_2$O (3×120 mL). The organic layer was dried over Na$_2$SO$_4$, filtered and concentrated. Flash silica gel chromatography eluting with EtOAc/hexane (3:7) afforded 404 mg (73.6%) as a yellow solid.

Step I: Preparation of 2,3-Ethylenedioxy-6-hydroxymethyl-9-hydroxy-12-(β-D-glucopyranosyl)-6,7,12,13-tetrahydroindolo[2,3-a]pyrrolo[3,4-c]carbazole-5,7-dione (9)

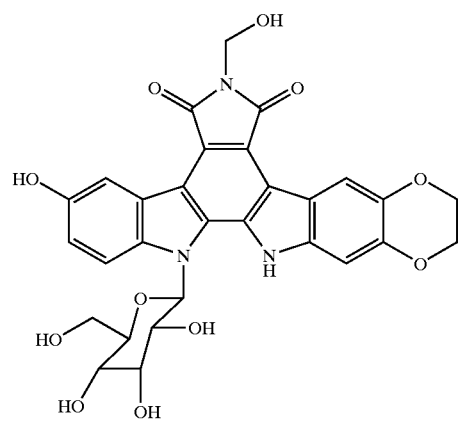

To a solution of 8 (140 mg, 0.1236 mmol) in HOAc (25 mL) was added palladium hydroxide [Pd(OH)$_2$, 140 mg]. The reaction was shaken under a hydrogen atmosphere (50 psi) at ambient temperature for 63 hours. The mixture was filtered through an Acrodisc syringe filter and concentrated in vacuo to give a crude solid. Flash chromatography eluting with MeOH/HOAc/EtOAc (12/1/87) afforded 42.0 mg (57.5%) as a yellow solid.

Step J: Synthesis of 2,3-Ethylenedioxy-9-hydroxy-12-(β-D-glucopyranosyl)-6,7,12,13-tetrahydroindolo[2,3-a]pyrrolo[3,4-c]carbazole-5,7-dione (Ia)

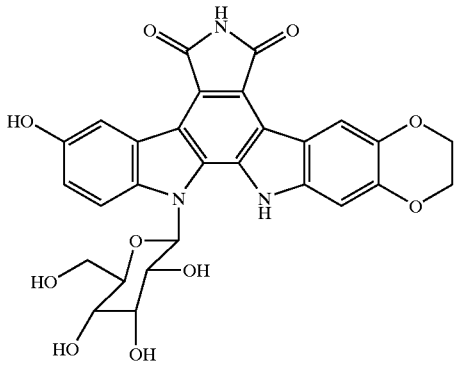

To a solution of 9 (5.0 mg, 0.00845 mmol) in MeOH (0.5 mL) was added NH$_4$OH (1.5 mL). The mixture was stirred at ambient temperature for 3 hours, then concentrated in vacuo to give a crude solid. Recrystallization with MeOH/hexane/CHCl$_3$ afforded 4.3 mg (90.5%) as a yellow solid.

EXAMPLE 2

Synthesis of 2,3-Methylenedioxy-9-hydroxy-12-(β-D-glucopyranosyl)-6,7,12,13-tetrahydroindolo[12,3-a]pyrrolo[3,4-c]carbazole-5,7-dione (Ib)

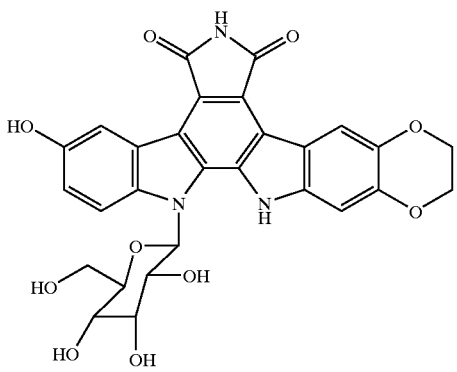

Step A: Preparation of 3,4-Methylenedioxytoluene (10)

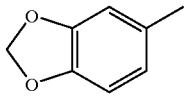

A mixture of 4-methylcatechol (26.0 g, 209.4 mmol) and NaOH (18.4 g, 461.0 mmol) in CH$_2$Cl$_2$ (40.0 mL) was heated to 100° C. under nitrogen for 2 hours. The solution was allowed to cool to ambient temperature and diluted with ethyl acetate (500 mL). The mixture was washed with NaHCO$_3$ (200 mL) and H$_2$O (2×200 mL). The organic layer was dried over Na$_2$SO$_4$, filtered and concentrated to give a crude oil. Flash chromatography eluting with hexane (100%) gradient to ether/hexane (1:1) afforded the title intermediate as a colorless oil 20.5 g (71.9%).

Step B: Preparation of 2-Nitro-4,5-methylenedioxytoluene (11)

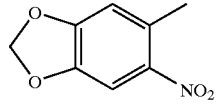

To a solution of 10 (19.0 g, 139.6 mmol) in acetic acid (180 mL) was added a solution of fuming HNO$_3$ (10 mL) in acetic acid (70 mL) dropwise over 30 minutes. The mixture was stirred at ambient temperature for 10 minutes, then poured into a beaker containing ice to give a crystalline precipitate, which was collected by vacuum filtration and washed with water to afford the crude product. Further purification via recrystallization from CH$_2$Cl$_2$/hexane gave the pure product (16.3 g, 64.4%).

Step C: Preparation of (E)-4,5-Methylenedioxy-2-nitro-1-pyrrolidinostyrene (12)

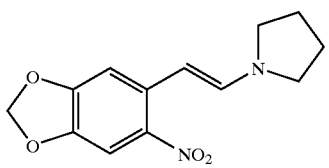

A solution of 11 (15.7 g, 86.74 mmol), N,N-dimethylformamide dimethyl acetal (15.5 g, 130.1 mmol) and pyrrolidine (9.25 g, 130.1 mmol) was heated to 110° C. and stirred for 3 hours under nitrogen. The reaction mixture was cooled, and a mixture of absolute methanol and ethanol (1:1; 250 mL) was added. The product crystallized as a bright red solid. Recovery by suction filtration afforded the product (16.2 g, 71.4%).

Step D: Preparation of 5,6-Methylenedioxyindole (13)

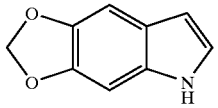

To a solution of 12 (15.7 g, 59.92 mmol) in methanol and THF (200 mL, 1:1) was added Raney nickel (1.5 mL) and hydrazine hydrate (3×2.56 mL, 240 mmol) in three equal portions every half hour at ambient temperature under nitrogen. The solution was then heated at 45° C. for two hours. The mixture was cooled to room temperature and the catalyst was removed by filtration through a bed of Celite, then washed three times with methylene chloride. The filtrate was evaporated and the residue dried by azeotroping with toluene (100 mL) to provide a crude oil. Flash silica gel column chromatography eluting with hexane (100%) gradient to ethyl acetate/hexane (30/70%) afforded the title intermediate as an off-white solid (5.1 g, 52.9%).

Step E: Preparation of 2-(4,5-Methylenedioxy-1H-indole-3-yl)-3-[5-benzyloxy-1-(2,3,4,5-tetra-O-benzyl-β-D-glucopyranosyl)-1H-indol-3-yl]-N-benzyloxymethyl Maleimide (14)

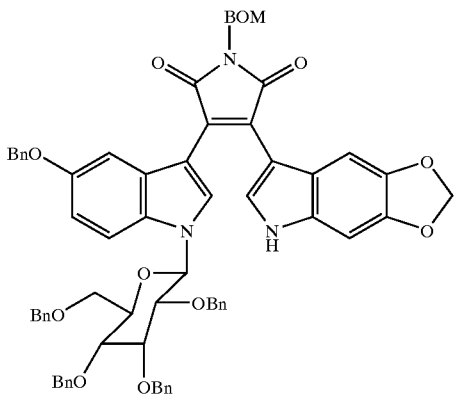

To a solution of 13 (279.0 mg, 1.73 mmol) in THF (35.0 mL) was added lithium hexamethyldisilazide (LiHMDS, 3.46 mL, 3.46 mmol, 1 M in THF) at 0° C. and stirred for 40 minutes. A solution of 6 in THF (20 mL) was added slowly to above mixture, followed by stirring for 20 minutes at 0° C. The mixture was diluted with EtOAc (350 mL), washed with HCl (1 M), NaHCO$_3$, brine, and H$_2$O. The organic layer was dried over Na$_2$SO$_4$, filtered and concentrated to give a crude mixture. Flash silica gel column chromatography eluting with hexane (100%) gradient to ethyl acetate/hexane (40/60%) afforded the title intermediate as a red solid 0.73 g (45.3%).

Step F: Preparation of 2,3-Methylenedioxy-6-benzyloxymethyl-9-benzyloxy-12-(2,3,4,5-tetra-O-benzyl-β-D-glucopyranosyl)-6,7,12,13-tetrahydroindolo[12,3-a]pyrrolo[3,4-c]carbazole-5,7-dione (15)

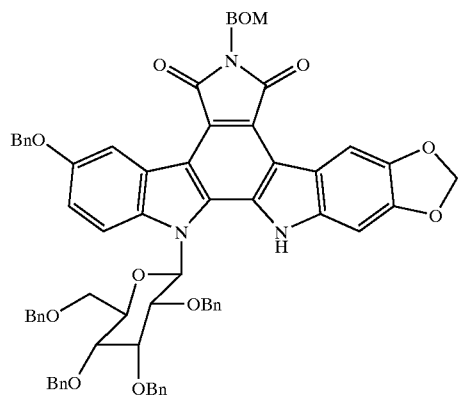

To a solution of 14 (650 mg, 0.58 mmol) in DMF (36 mL) was added palladium(II) trifluoroacetate (405 mg, 1.22 mmol), and the reaction was stirred at 80° C. for one hour. The solution was cooled to room temperature and diluted with EtOAc (350 mL), then washed with HCl (1 M), NaHCO$_3$, brine (150 mL) and H$_2$O (3×150 mL). The organic layer was dried over Na$_2$SO$_4$, filtered and concentrated. Flash silica gel column chromatography eluting with EtOAc/hexane (3:7) afforded 248 mg (38.2%) as a yellow solid.

Step G: Preparation of 2,3-Methylenedioxy-6-hydroxymethyl-9-hydroxy-12-(β-D-glucopyranosyl)-6,7,12,13-tetrahydroindolo[2,3-a]pyrrolo[3,4-c]carbazole-5,7-dione (16)

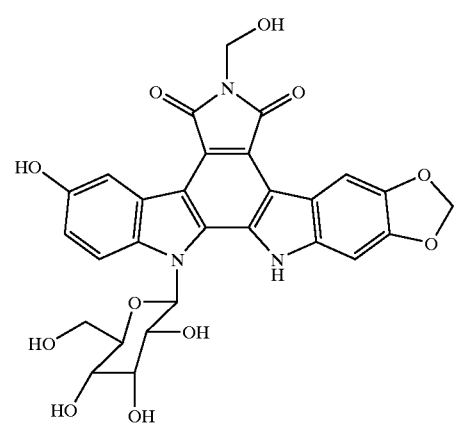

To a solution of 15 (150 mg, 0.1341 mmol) in HOAc (10 mL) was added palladium hydroxide (150 mg). The reaction was shaken under an atmosphere of H$_2$ (50 psi) at ambient temperature for 60 h. The mixture was filtered through an Acrodisc syringe filter and concentrated in vacuo to give a crude solid. Flash silica gel column chromatography eluting with MeOH/AcOH/EtOAc (12/1/87) afforded 56.2 mg (76.7%) as a yellow solid.

Synthesis of 2,3-Methylenedioxy-9-hydroxy-12-(β-D-glucopyranosyl)-6,7,12,13-tetrahydroindolo[2,3-a]pyrrolo[3,4-c]carbazole-5,7-dione (Ib)

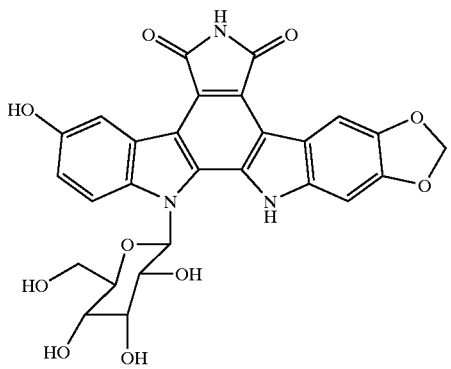

To a solution of 16 (30.0 mg, 0.052 mmol) in MeOH (2.0 mL) was added NH₄OH (4.0 mL). The mixture was stirred at ambient temperature for 3 hours, then concentrated in vacuo to give a crude solid. Flash silica gel column chromatography eluting with MeOH/AcOH/EtOAc (12/1/87) afforded 26.1 mg (91.1%) as a yellow solid.

EXAMPLE 3

Synthesis of 2,3-(Isopropylenedioxy)-9-hydroxy-13-(β-D-glucopyranosyl)-6,7,12,13-tetrahydroindolo[2,3-a]pyrrolo[3,4-c]carbazole-5,7-dione (Ic)

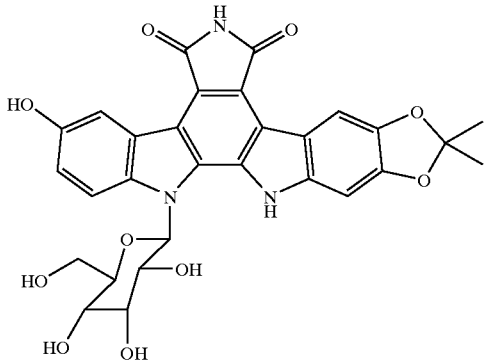

Step A: Preparation of 4-Methyl-2',2'-dimethyl-1,3-benzodioxole (17)

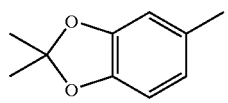

A mixture of 4-methylcatechol (75.0 g, 604.2 mmol, Aldrich), phosphorous pentoxide (85.8 g, 302.3 mmol) in acetone (200 mL) and toluene (200 mL) was refluxed under nitrogen for 50 hours. The solution was allowed to cool to ambient temperature and diluted with ether (500 mL). The mixture was washed with 2 M NaOH (2×200 mL) and H₂O (2×200 mL). The organic layer was dried over Na₂SO₄, filtered and concentrated to give a crude oil. Flash chromatography eluting with hexane (100%) gradient to ether/hexane (1:1) afforded the title intermediate as a colorless oil (82.0 g, 82.7%).

Step B: Preparation of 4-Methyl-5-nitro-2',2'-dimethyl-1,3-benzodioxole (18)

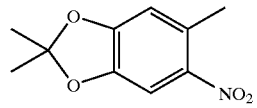

To a solution of 17 (65.0 g, 395.9 mmol) in HOAc (450 mL) was added a solution of fuming HNO₃ (35 mL) in acetic acid (100 mL) over 30 minutes. The mixture was stirred at ambient temperature for 10 minutes, then poured into a beaker containing ice to give a crystalline precipitate which was collected by vacuum filtration and washed with water to afford the crude product (77.1 g, 93.8%).

Step C: Preparation of (E)-4,5-(Isopropylenedioxy)-2-nitro-1-pyrrolidinostyrene (19)

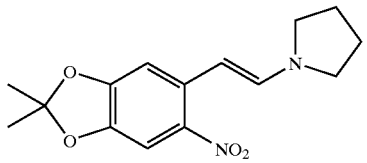

A solution of 18 (45 g, 215.1 mmol), N,N-dimethylformnamide dimethyl acetal (38.45 g, 322.7 mmol) and pyrrolidine (22.95 g, 322.7 mmol) were heated to 110° C. and stirred for 16 hours under nitrogen. The reaction mixture was cooled, and a mixture of absolute methanol and ethanol (1:1; 600 mL) was added. The product crystallized as a bright red solid. Recovery by suction filtration afforded the product (51.0 g, 81.5%).

Step D: Preparation of 5,6-(Isopropylenedioxy)indole (20)

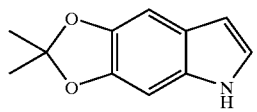

To a solution of 19 (50.0 g, 171.7 mmol) in methanol and THF (400 mL, 1:1) was added Raney nickel (4.0 mL) and hydrazine hydrate (3×7.13 mL, 686.6 mmol) in three equal portions every minutes at ambient temperature under nitrogen. The solution was heated at 45° C. for two hours. The mixture was cooled to room temperature and the catalyst was removed by filtration through a bed of Celite, then washed three times with methylene chloride. The filtrate was evaporated and the residue dried azeotropically with toluene (100 mL) to give a crude oil. Flash silica gel column chromatography eluting with hexane (100%) gradient to ethyl acetate/hexane (30/70%) afforded the title intermediate as an off-white solid, which was futher purified via recrystallization with benzene/petroleum ether (2:8) to give the pure product (15.1 g, 46.2%).

Step E: Preparation of 3-[(4,5-Isopropylenedioxy-1H-indol-3-yl)]-4-[5-benzyloxy-1-(2,3,4,5-tetra-O-benzyl-β-D-glucopyranosyl)-1H-indol-3-yl]-N-benzyloxymethyl Maleimide (21)

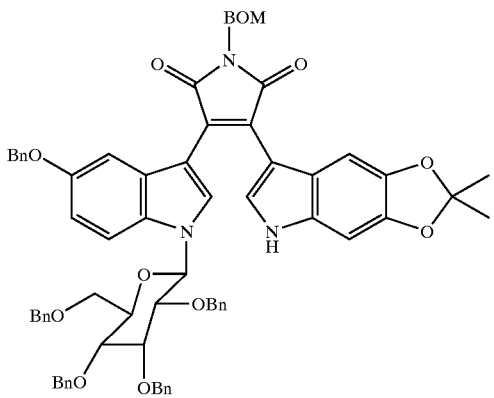

To a solution of 20 (2.27 mg, 12.02 mmol) in THF (150 mL) was added lithium hexamethyldisilazide (LiHMDS, 12.02 mL, 12.02 mmol, 1 M in THF) at 0° C. and the solution was stirred for 40 minutes. A solution of 6 (5.0 g, 4.81 mmol) in THF (50 mL) was added slowly to the above mixture, followed by stirring for 20 minutes at 0° C. The mixture was diluted with EtOAc (400 mL), then washed with HCl (1 M), NaHCO₃, brine, and H₂O. The organic layer was dried over Na₂SO₄, filtered and concentrated to give a crude mixture. Flash silica gel column chromatography eluting with hexane (100%) gradient to ethyl acetate/hexane (40/60%) afforded the title intermediate as a red solid (3.02 g, 54.71%).

Step F: Preparation of 2,3-Isopropylenedioxy-6-benzyloxymethyl-9-benzyloxy-12-(2,3,4,5-tetra-O-benzyl-β-D-glucopyranosyl)-6,7,12,13-tetrahydroindolo[2,3-a]pyrrolo[3,4-c]carbazole-5,7-dione (22)

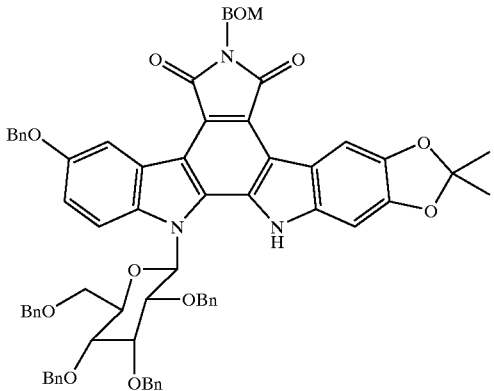

To a solution of 21 (1.60 g, 1.39 mmol) in DMF (85 mL) was added palladium(II) trifluoroacetate (657 mg, 2.93 mmol), and the solution was stirred at 80° C. for two hours.

The solution was cooled to room temperature and diluted with EtOAc (250 mL), then washed with HCl (1 M), NaHCO₃, brine (150 mL), and H₂O (3×150 mL). The organic layer was dried over Na₂SO₄, filtered and concentrated. Flash silica gel column chromatography eluting with EtOAc/hexane (3:7) afforded 1.02 g (63.7%) as a yellow solid.

Step G: Preparation of 2,3-Isopropylenedioxy-6-hydroxymethyl-9-hydroxy-12-(β-D-glucopyranosyl)-6,7,12,13-tetrahydroindolo[2,3-a]pyrrolo[3,4-c]carbazole-5,7-dione (23)

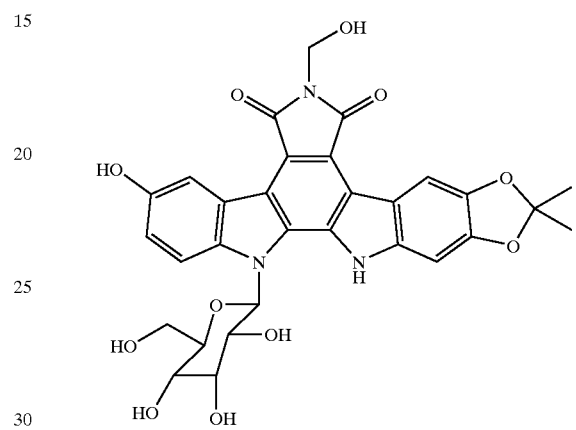

To a solution of 22 (280 mg, 0.244 mmol) in HOAc (12 mL) was added palladium hydroxide (100 mg). The reaction was shaken under an atmosphere of H₂ (50 psi) at ambient temperature for 60 h. The mixture was filtered through an Acrodisc syringe filter and concentrated in vacuo to give a crude solid. Flash silica gel column chromatography eluting with MeOH/AcOH/EtOAc (12/1/87) afforded 135 mg (91.4%) as a yellow solid.

Step H: Synthesis of 2,3-Isopropylenedioxy-9-hydroxy-12-(β-D-glucopyranosyl)-6,7,12,13-tetrahydroindolo[2,3-a]pyrrolo[3,4-c]carbazole-5,7-dione (Ic)

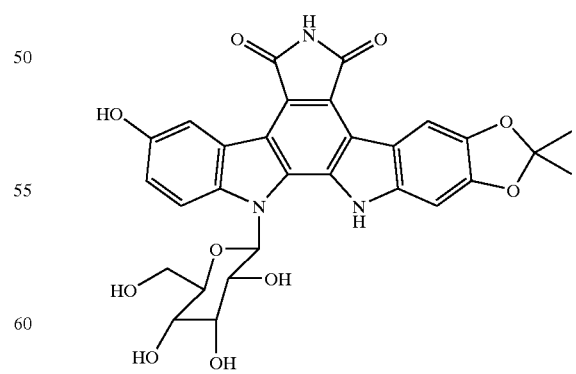

To a solution of 23 (100.0 mg, 0.165 mmol) in MeOH (7.0 mL) was added NH₄OH (6.0 mL). The mixture was stirred at ambient temperature for 2 hours, then concentrated in vacuo to give a crude solid. Flash silica gel column chromatography eluting with MeOH/HOAc/EtOAc (12/1/87) afforded 81.0 mg (85.3%) as a yellow solid.

EXAMPLE 4

Synthesis of 2,3-Dimethoxy-9-hydroxy-13-(β-D-glucopyranosyl)-6,7,12,13-tetrahydroindolo[2,3-a]pyrrolo[3,4-c]carbazole-5,7-dione (Id)

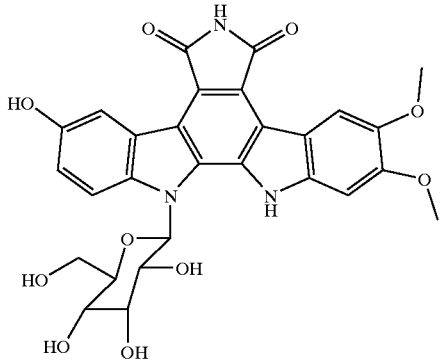

Step A: Preparation of 3-[(4,5-Dimethoxy-1H-indol-3-yl)]-4-[5-benzyloxy-1-(2,3,4,5-tetra-O-benzyl-β-D-glucopyranosyl)-1H-indol-3-yl] -N-benzyloxymethyl Maleimide (24)

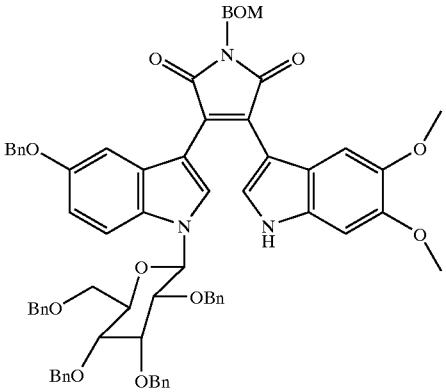

To a solution of 5,6-dimethoxyindole (441 mg, 2.49 mmol) in THF (50 mL) was added lithium hexamethyldisilazide (LiHMDS, 4.98 mL, 4.98 mmol, 1 M in THF) at 0° C. and the solution was stirred for 40 minutes. A solution of 6 (2.25 g, 2.16 mmol) in THF (30 mL) was added slowly to the above mixture, followed by stirring for 20 minutes at 0° C. The mixture was diluted with EtOAc (250 mL), then washed with HCl (1 M), NaHCO₃, brine, and H₂O. The organic layer was dried over Na₂SO₄, filtered and concentrated to give a crude mixture. Flash silica gel column chromatography eluting with hexane (100%) gradient to ethyl acetate/hexane (60/40%) afforded the title intermnediate as a red solid (2.79 g, 98.6%).

Step B: Preparation of 2,3-Dimethoxy-6-benzyloxymethyl-9-benzyloxy-12-(2,3,4,5-tetra-O-benzyl-β-D-glucopyranosyl)-6,7,12,13-tetrahydroindolo[2,3-a]pyrrolo[13,4-c]carbazole-5,7-dione (25)

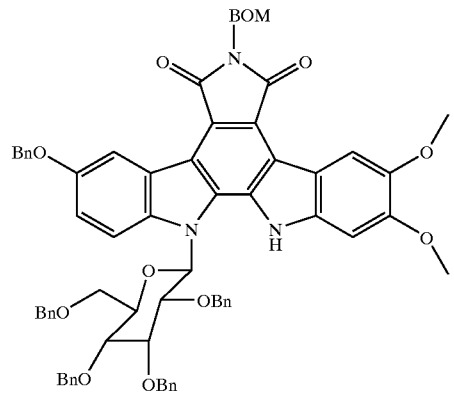

To a solution of 24 (1.50 g, 1.32 mmol) in DMF (60 mL) was added palladium(II) trifluoroacetate (923 mg, 2.77 mmol), and the solution was stirred at 80° C. for two hours. The solution was cooled to room temperature and diluted with EtOAc (250 mL), then washed with HCl (1 M), NaHCO₃, brine (150 mL), and H₂O (3×150 mL). The organic layer was dried over Na₂SO₄, filtered and concentrated. Flash silica gel column chromatography eluting with EtOAc/hexane (3:7) afforded 769 mg (51.4%) as a yellow solid.

Step C: Synthesis of 2,3-Isopropylenedioxy-9-hydroxy-12-(β-D-glucopyranosyl)-6,7,12,13-tetrahydroindolo[2,3-a]pyrrolo[3,4-c]carbazole-5,7-dione (Id)

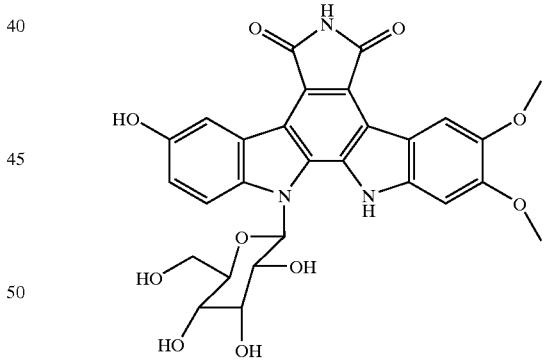

To a solution of 25 (600 mg, 0.529 mmol) in HOAc (25 mL) was added palladium hydroxide (600 mg). The reaction was shaken under an atmosphere of H₂ (50 psi) at ambient temperature for 60 hours in a Parr shaker. The solution was filtered through an Acrodisc syringe filter and concentrated in vacuo to provide a solid. The solid was dissolved in MeOH (150 mL) and aqueous NH₄OH (50 mL). The mixture was stirred at ambient temperature for 1.5 hours, then concentrated in vacuo to provide the crude product. Flash silica gel chromatography eluting with MeOH/HOAc/EtOAc (12/1/87) afforded 166 mg (60.0%) of desired product as a yellow solid.

EXAMPLE 5

Synthesis of 2,3-Ethylenedioxy-9-hydroxy-13-(β-D-glucopyranosyl)-6,7,12,13-tetrahydroindolo[2,3-a]pyrrolo[3,4-c]carbazole-5,7-dione (IIa)

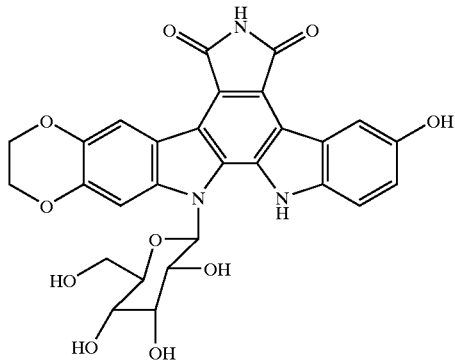

Step A: Preparation of 3-Bromo-4-(4,5-ethylenedioxy-1H-indol-3-yl)-N-benzyloxymethylmaleimide (26)

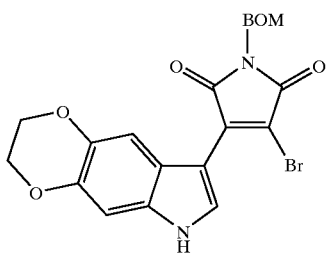

To a solution of 4 (2.1 g, 12.0 mmol) in benzene (100 mL) was added methylmagnesium iodide (4.4 mL, 13.19 mmol, 3 M in ether) at 0° C. After stirring for one hour, a solution of N-benzyloxymethyl-3,4-dibromomaleimide (4.5 g, 12.0 mmol) in benzene (30 mL) and THF (50 mL) was added slowly. The reaction mixture was stirred at 0° C. for 30 minutes and then warmed to room temperature for one hour. The mixture was diluted with EtOAc (250 mL), then washed with HCL (100 mL, 0.3 M), NaHCO₃ (100 mL) and H₂O (100 mL). The organic layer was dried over Na₂SO₄, filtered and concentrated. Flash silica gel chromatography, eluting with a hexane gradient to EtOAc/hexane (3:2) afforded the title intermediate as a yellow solid (2.83 g, 50.5%)

Step B: Preparation of 3-Bromo-4-[4,5-ethylenedioxy-1-(2,3,4,5-tetra-O-benzyl-β-D-glucopyranosyl)-1H-indol-3-yl]-N-benzyloxymethylmaleimide (27)

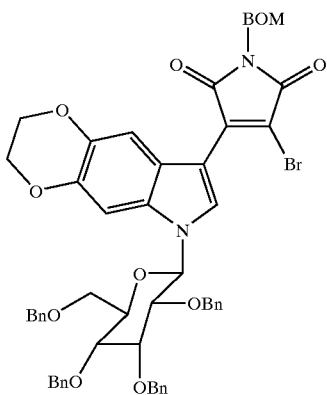

To a solution of 26 (2.7 g, 5.75 mmol), 2,3,4,5-tetra-O-benzyl-D-glucopyranose (9.33 g, 17.26 mmol) and triph-enylphosphine (4.53 g, 17.26 mmol) in THF (150 mL) at −78° C. was added diisopropylazodicarboxylate (DIAD) (3.4 mL, 17.26 mmol) dropwise. Stirring was continued at −78° C. for 3 hours, then the solution was warmed to 0° C. with the aid of a ice-water bath and stirring continued for 2 hours. The mixture was diluted with EtOAc (300 mL), then washed with HCL, brine and H₂O. The organic layer was dried over Na₂SO₄, filtered and concentrated. Flash silica gel chromatography, eluting with a toluene gradient to toluene/EtOAc (25:1) afforded the title intermediate as a yellow solid 3.15 g (55.3%).

Step C: Preparation of 3-(5-Benzyloxy-1H-indol-3-yl)-4-[4,5-ethylenedioxy-1-(2,3,4,5-tetra-O-benzyl-β-D-glucopyranosyl)-1H-indol-3-yl]-N-benzyloxymethylmaleimide (28)

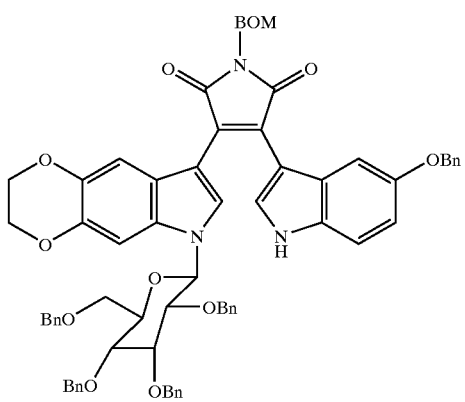

To a solution of 5-benzyloxyindole (1.52 g, 6.8 mmol) in THF (70.0 mL) was added lithium hexamethyldisilazide (LiHMDS, 6.8 mL, 6.8 mmol, 1 M in THF) at 0° C., and the solution stirred for 30 minutes. A solution of 27 in THF (80 mL) was added slowly to the above mixture, followed by stirring for 30 minutes at 0° C. The mixture was diluted with EtOAc (300 mL), then washed with HCl (1 M), NaHCO₃, brine, and H₂O. The organic layer was dried over Na₂SO₄, filtered and concentrated to give the crude product. Flash silica gel chromatography eluting with a hexane (100%) gradient to EtOAc/hexane (2:3) afforded the title intermediate as a red solid 1.62 g (52.6%).

Step D: Preparation of 2,3-Ethylenedioxy-6-benzyloxymethyl-9-benzyloxy-13-(2,3,4,5-tetra-O-benzyl-β-D-glucopyranosyl)-6,7,12,13-tetrahydroindolo[2,3-a]pyrrolo[3,4-c]carbazole-5,7-dione (29)

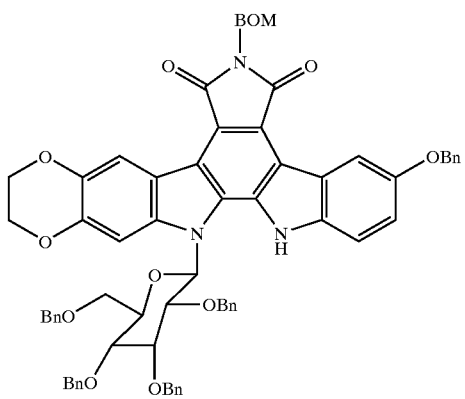

To a solution of 28 (1.0 g, 0.882 mmol) in DMF (50 mL) was added palladium(II) trifluoroacetate (615.4 mg, 1.85 mmol), and the solution was stirred at 80° C. for 1 hour. The solution was cooled to room temperature and diluted with EtOAc (350 mL), then washed with HCl (1 M), NaHCO₃, brine (150 mL) and H₂O (3×150 mL). The organic layer was dried over Na₂SO₄, filtered and concentrated. Flash silica gel chromatography eluting with EtOAc/hexane (3:7) afforded 471.0 g (47.2%) of desired product as a yellow solid.

Step E: Synthesis of 2,3-Ethylenedioxy-9-hydroxy-13-(β-D-glucopyranosyl)-6,7,12,13-tetrahydroindolo[2,3-a]pyrrolo[3,4-c]carbazole-5,7-dione (IIa)

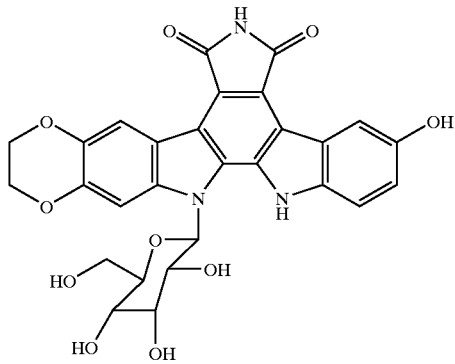

To a solution of 29 (350 mg, 0.309 mmol) in HOAc (12 mL) was added palladium hydroxide (350 mg). The reaction was shaken under an atmosphere of H₂ (50 psi) at ambient temperature for 62 hours in a Parr shaker. The solution was filtered through an Acrodisc syringe filter and concentrated in vacuo to provide a solid. The solid was dissolved in MeOH (200 mL) and aqueous NH₄OH (10 mL). The mixture was stirred at ambient temperature for 3 hours, then concentrated in vacuo to provide the crude product. Flash silica gel chromatography eluting with MeOH/HOAc/EtOAc (12/1/87) afforded 164 mg (94.5%) of desired product as a yellow solid.

EXAMPLE 6

Synthesis of 2,3-Methylenedioxy-9-hydroxy-13-(β-D-glucopyranosyl)-6,7,12,13-tetrahydroindolo[2,3-a]pyrrolo[3,4-c]carbazole-5,7-dione (IIb)

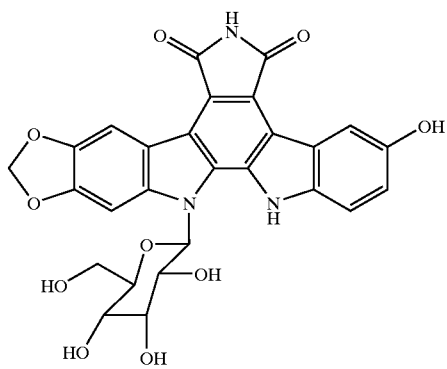

Step A: Preparation of 3-Bromo-4-(5,6-methylenedioxy-1H-indol-3-yl)-N-benzyloxymethylmaleimide (30)

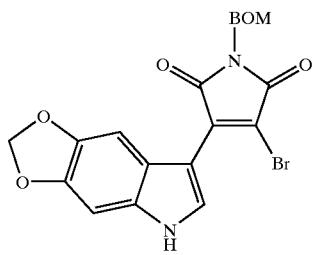

To a solution of 13 (2.7 g, 16.75 mmol) in benzene (100 mL) was added methylmagnesium iodide (6.14 mL, 18.42 mmol, 3 M in ether) at 0° C. The solution was stirred for 1 hour, and then a solution of N-benzyloxymethyl-3,4-dibromomaleimide (6.28 g, 16.75 mmol) in benzene (30 mL) and THF (50 mL) was added slowly. The reaction mixture was stirred at 0° C. for 30 minutes, then warmed to room temperature and stirred for 1 hour. The mixture was diluted with EtOAc (200 mL), then washed with HCL (100 mL, 0.3 M), NaHCO₃ (100 mL) and H₂O (100 mL). The organic layer was dried over Na₂SO₄, filtered and concentrated. Crystallization of the crude oil with MeOH afforded the title intermediate as a yellow solid (2.92 g, 38.2%).

Step B: Preparation of 3-Bromo-4-[5,6-methylenedioxy-1-(2,3,4,5-tetra-O-benzyl-β-D-glucopyranosyl)-1H-indol-3-yl]-N-benzyloxymethylmaleimide (31)

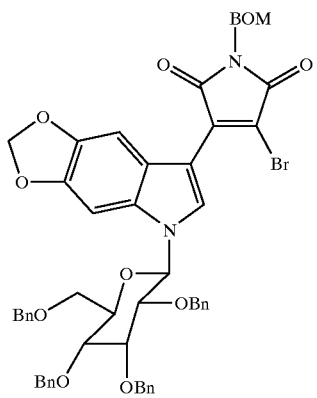

To a solution of 30 (2.3 g, 5.05 mmol), 2,3,4,5-tetra-O-benzyl-D-glucopyranose (8.2 g, 15.2 mmol) and triphenylphosphine (4.0 g, 15.2 mmol) in THF (150 mL) at −78° C. was added diisopropylazodicarboxylate (DIAD) (2.98 mL, 15.2 mmol) dropwise. The solution was stirred at −78° C. for 3 hours, then warmed to 0° C. and stirred further for 2 hours. The mixture was diluted with EtOAc (300 mL), then washed with HCl, brine, and H₂O. The organic layer was dried over Na₂SO₄, filtered and concentrated. Flash silica gel chromatography eluting with a toluene gradient to toluene/EtOAc (25:1) afforded the title intermediate as a yellow solid 3.05 g (61.8%).

Step C: Preparation of 3-(5-Benzyloxy-1H-indol-3-yl)-4-[5,6-methylenedioxy-1-(2,3,4,5-tetra-O-benzyl-β-D-glucopyranosyl)-1H-indol-3-yl]-N-benzyloxymethylmaleimide (32)

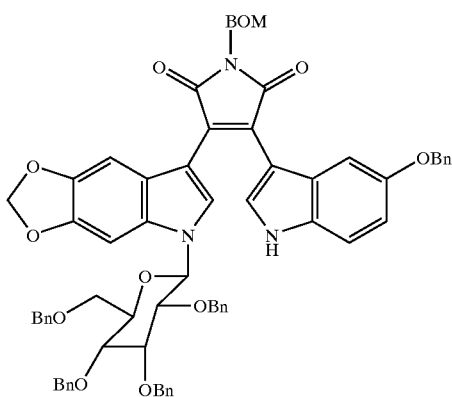

To a solution of 5-benzyloxyindole (822.0 mg, 3.68 mmol) in THF (35 mL) was added lithium hexamethyldisilazide (LiHMDS, 3.68 mL, 3.68 mmol, 1 M in THF) at 0° C., and the resulting solution was stirred for 40 minutes. A solution of 31 in THF (20 mL) was added slowly to the above mixture, followed by stirring for 20 minutes at 0° C. The mixture was diluted with EtOAc (300 mL), then washed with HCl (1 M), NaHCO$_3$, brine, and H$_2$O. The organic layer was dried over Na$_2$SO$_4$, filtered and concentrated to provide the crude product. Flash silica gel chromatography eluting with a hexane (100%) gradient to EtOAc/hexane (2:3) afforded the title intermediate as a red solid (1.56 g, 91.2%).

Step D: Preparation of 2,3-Methylenedioxy-6-benzyloxymethyl-9-benzyloxy-13-(2,3,4,5-tetra-O-benzyl-β-D-glucopyranosyl)-6,7,12,13-tetrahydroindolo[2,3-a]pyrrolo[3,4-c]carbazole-5,7-dione (33)

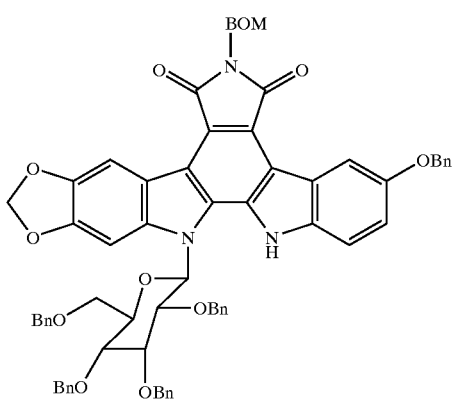

To a solution of 32 (1.45 g, 1.294 mmol) in DMF (75 mL) was added palladium(II) trifluoroacetate (904 mg, 2.72 mmol), and the solution was stirred at 80° C. for 1 hour. The solution was cooled to room temperature and diluted with EtOAc (350 mL), then wash with HCl (1 M), NaHCO$_3$, brine, and H$_2$O (3×150 mL). The organic layer was dried over Na$_2$SO$_4$, filtered and concentrated. Flash silica gel chromatography eluting with EtOAc/hexane (3:7) afforded 1.05 g (72.6%) of the desired product as a yellow solid.

Step E: Synthesis of 2,3-Methylenedioxy-9-hydroxy-13-(β-D-glucopyranosyl)-6,7,12,13-tetrahydroindolo[2,3-a]pyrrolo[3,4-c]carbazole-5,7-dione (IIb)

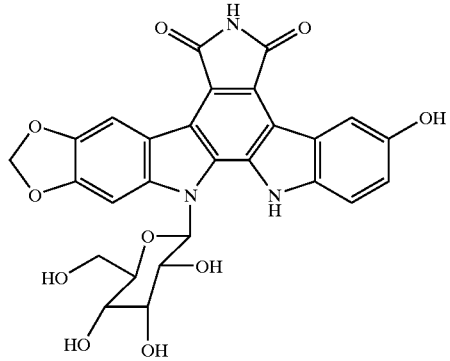

To a solution of 33 (300 mg, 0.268 mmol) in HOAc (14 mL) was added palladium hydroxide (300 mg). The reaction was shaken under an atmosphere of H$_2$ (50 psi) at ambient temperature for 60 hours in a Parr shaker. The solution was filtered through an Acrodisc syringe filter and concentrated in vacuo to provide the crude product as a solid. The solid was dissolved in MeOH (20.0 mL) and aqueous NH$_4$OH (30.0 mL), stirred at ambient temperature for 2 hours, and then concentrated in vacuo to provide the crude product. Flash silica gel chromatography eluting with MeOH/HOAc/EtOAc (12/1/87) afforded 92.0 mg (62.7%) as a yellow solid.

EXAMPLE 7

Typical Experimental Procedure for the Synthesis Compounds with the Following General Formula

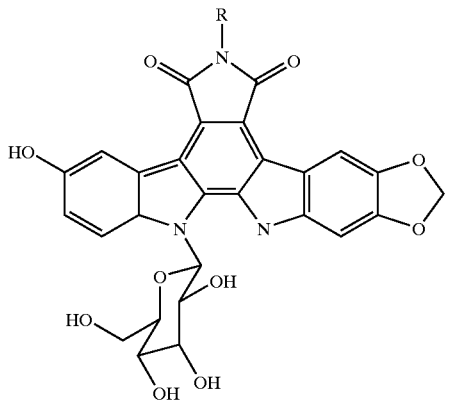

To a solution of the anhydride YPX-2-21 (32 mg, 0.05834 mmol) in DMF (1.8 mL) was added appropriate hydrazine or amine [0.5834 mmol] (see Table 1). The reaction was placed under atmosphere of nitrogen at 95° C. for 2 h. The mixture was diluted with water (12 mL) and stirred at 0° C. for two h. The precipitate was filtered and washed with water and ethyl ether to obtain the product (see Table 1 for yields).

TABLE 1

| S. No. | R | Yield % |
|---|---|---|
| 1 | —NH$_2$ | 72 |
| 2 | ⌁N⌁OH | 27.4 |

TABLE 1-continued

| S. No. | R | Yield % |
|---|---|---|
| 3 | -N(Me)-CH2-CH2-CN | 68 |
| 4 | -N(Me)-C(=O)-O-CH2-CH2-OH | 76 |
| 5 | -CH2-C(=O)-CH2-CN | 87.2 |
| 6 | -CH(CH2CH3)(CH2OH) with -OH (diol branched) | 90.2 |
| 7 | -CH2CH2CH2-morpholinyl | 66.4 |
| 8 | -CH2CH2CH2-OH | 27.4 |
| 9 | -N(Me)-S(=O)2-CH3 | 52 |
| 10 | -N(Me)-C(=O)-2-furyl | 84 |
| 11 | -N(Me)-C(=O)-2-thienyl | 100 |
| 12 | -CH2CH2CH2-piperazinyl | 69.4 |
| 13 | -N(Me)-C(=O)-(5-OMe-pyrimidin-2-yl) | 70.4 |
| 14 | -N(Me)-C(=O)-CH(OH)-CH(OH)-CH(OH)-CH(OH)-CH2OH | 54 |
| 15 | -N(Me)-C(=O)-(3,5-dihydroxyphenyl) | 67.6 |
| 16 | —CHO | 76 |

EXAMPLE 8

Biological Evaluation a.) Topoisomerase I assay. Reaction buffer (10.3 μL H$_2$O, 2.0 μL 10×buffer, 1.5 μL 100 μM MgCl$_2$, and 3.2 μL 500 mM KCl) was prepared and kept on ice. 10×Buffer was prepared by mixing 2 mL 2M Tris pH 7.5, 15.3 μL 10% DTT, 100 μL 0.5 M EDTA, 75 μL 20 mg/mL BSA, and 7.935 μL H$_2$O. Test poisons were prepared in DMSO at such concentrations that the final incubation mixture was 5% DMSO. DNA mix was prepared by dissolving 55 mL of pHOT1 DNA solution (0.25 μg/μL) with 715 μL reaction buffer. Topo I mix was prepared by mixing 14 μL of Topo I solution (2 units/μL) with 266 μL of reaction buffer. Proteinase K solution was prepared fresh as 10 mg/mL in 1% SDS. Gel loading buffer was prepared by dissolving 1 mg bromophenol blue in 100 μL H$_2$O, then adding 900 μL 50% glycerol. Topotecan (Camptosar) and 3,9-dihydroxy-12-(β-D-glucopyranosyl)-6,7,12,13-tetrahydroindolo[2,3-a]pyrrolo[3,4-c]carbazole-5,7-dione[11] (ALS-007) were used as positive controls.

The assay was conducted as follows. DNA mix (14 μL) was added to sample tubes containing 1 μL of test poison solution and stored on ice. Next, 5 μL of Topo I mix was added, the solution was mixed with the pipettor, then incubated with gentle rocking in a 37° C. water bath for 30 minutes. The reactions were stopped via addition of 2 μL of proteinase K solution, and incubation was continued for another 30 minutes, then placed on ice. 2.2 μL of 5 M NaCl and 75 μL of EtOH were added to the tubes, the tubes were vortexed briefly, then placed on dry ice for 1 hour. The DNA was pelleted by centrifugation at 16,000×g for 10 minutes at 4° C. EtOH was removed from each tube using a gel loading pipette tip, and the DNA pellet was re-suspended in 18 μL of reaction buffer and 2 μL of gel loading buffer. The samples were vortexed briefly, then spun for 15 seconds in a micro-centrifuge to force all the liquid to the bottom of the tubes. The samples were loaded onto a 1% agarose gel made with 1×TBE containing 2 μg/mL chloroquine. The gels were run at 35 V for 15 hours in 1×TBE. Gels were stained with 0.5 μg/mL ethidium bromide in 1×TBE for 1 hour, then destained for 30 minutes in H$_2$O. Gels were photographed with a digital camera, and the digitized images analyzed using NIH software. IC$_{50}$ values were determined by comparing supercoiled DNA band density (negative controls containing 5 μL reaction buffer in place of Topo I mix) with the supercoiled DNA bands remaining in the test samples.

TABLE 2

Poisoning of Human Topoisomerase I by Indolocarbazole Analogues

| Agent | IC$_{50}$ (μM) |
|---|---|
| Topotecan | 31.3 |
| ALS-007 | 20.9 |
| 9 | 3.9 |
| 16 | 3.6 |
| Ia | 5.4 |
| Ib | 3.6 |
| 23 | 130 |
| Ic | 8.1 |
| IIa | >400 |
| IIb | >400 | b.) In vitro Cytotoxicity Assay. 96-Well tissue culture cluster plates were seeded with 100 μL of cell suspension (5×10$^3$ cells/mL), and incubated overnight for cell anchorage and acclimation. Cells were propagated under sterile conditions in RPMI 1640 or DMEM with 10% fetal bovine serum, 2 mM L-glutamine, and sodium bicarbonate (complete medium), and incubated at 37° C. The test compounds were prepared in DMSO and then diluted in complete media. A range of eight concentrations was used for each test drug to establish cytotoxicity, with eight replicates for each concentration. All dosing was conducted using a Biomek 2000 robotic liquid handler. The plates were incubated at 37° C. with 5% $CO_2$ and 95% relative humidity. The data were analyzed for cytotoxicity using the MTS assay 3–5 days (depending upon the growth rate of the cell lines) after commencement of treatment. MTS (3-(4,5-dimethylthiazol-2-yl)-5-(3-carboxymethoxyphenyl)-2-(4-sulfophenyl)-2H-tetrazolium) is bio-reduced by viable cells into a soluble formazan that absorbs at 490 nm, allowing simple spectrophotometric measurement of viable cells. Topotecan (Camptosar) and 3,9-dihydroxy-12-(β-D-1-glucopyranosyl)-6,7,12,13-tetrahydroindolo[2,3-a]pyrrolo[3,4-c]carbazole-5,7-dione[11] (ALS-007) were used as positive controls.

c.) MTS Assay. A solution of 40 μL of MTS/PES solution (purchased from Promega Corporation) was added to each well, and incubated for one to four hours. The absorbance of formazan in each monolayer was measured at 490 nm on a Coulter microplate reader. The data were processed in a spreadsheet program to provide a dose-response curve, allowing determination of the $IC_{50}$.

TABLE 2

Growth-Inhibitory Activity Against Various Human Tumor Cell Lines

| Agent | $IC_{50}$ (μM) | | |
|---|---|---|---|
| | HT-29 Colon | DU-145 Prostate | OVCAR-3 Ovarian |
| Topotecan | 0.533 | 0.030 | <0.003 |
| ALS-007 | 9.96 | 0.338 | <0.01 |
| 9 | >10 | 0.718 | <0.01 |
| 16 | >10 | 0.549 | <0.01 |
| Ia | >10 | 0.845 | <0.01 |
| Ib | >10 | 0.460 | <0.01 |
| 23 | >10 | 3.52 | 0.043 |
| Ic | >10 | 2.36 | 0.036 |

As illustrated by the results in Table 3, in a side-by-side comparison, the compounds diclosed in this invention provide a stronger poisoning effect against human Topo I than the control compounds, topotecan (a clinically-used Topo I poison/antitumor agent) and ALS-007, an experimental indolocarbazole previously disclosed[11]. Additionally, in a side-by-side comparison, the compounds disclosed in this invention exhibit in vitro cytotoxicity profiles against a series of three human tumor cell lines similar to the two control compounds (Table 2).

CITATIONS (1) Champoux, J. J. *Adv. Pharmacol.* 1994, 29A, 71–82.
(2) Redinbo, M. R.; Stewart, L.; Kuhn, P.; Champoux, J. J.; Hol, W. G. J. *Science* 1998, 279, 1504–1513.
(3) Pommier, Y.; Tanizawa, A.; Kohn, K. W. *Adv. Pharmacol.* 1994, 29B, 73–92.
(4) Kojiri, K.; Kondo, H.; Arakawa, H.; Ohkubo, M.; Suda, H. U.S. Pat. No. 5,591,842 Jan. 7, 1997.
(5) Kojiri, K.; Kondo, H.; Arakawa, H.; Ohkubo, M.; Suda, H. U.S. Pat. No. 5,922,860 Jul. 13, 1999.
(6) Kojiri, K.; Kondo, H.; Arakawa, H.; Ohkubo, M.; Suda, H. U.S. Pat. No. 5,668,271 Sep. 16, 1997.
(7) Kojiri, K.; Kondo, H.; Arakawa, H.; Ohkubo, M.; Suda, H. U.S. Pat. No. 5,804,564 Sep. 8, 1998.
(8) Arakawa, H.; Iguchi, T.; Yoshinari, K.; Kojiri, K.; Suda, H.; Okura, A. *Jpn. J Cancer Res.* 1993, 84, 574–581.
(9) Arakawa, H.; Tomoko, I.; Masashi, M.; Yoshinari, T.; Katsuhisa, K.; Hiroyuki, S.; Okura, A.; Nishimura, S. *Cancer Res.* 1995, 55, 1316–1320.
(10) Yoshinari, T.; Ohkubo, M.; Fukasawa, K.; Egashira, S.; Hara, Y.; Matsumoto, M.; Nakai, K.; Arakawa, H.; Morishima, H.; Nishimura, S. *Cancer Res.* 1999, 59, 4271–4275.
(11) Zembower, D. E.; Zhang, H.; Lineswala, J. P.; Kuffel, M. J.; Aytes, S. A.; Ames, M. M. *Bioorg. Med. Chem. Lett.* 1999, 9, 145–150.
(12) Batcho, A. D.; Leimgruber, W. *Org. Synth. Coll.* Vol. VII 1990, 34–41.
(13) Kaneko, T.; Wong, H.; Okamoto, K. T.; Clardy, J. *Tetrahedron Lett.* 1985, 26, 4015–4018.
(14) Ohkubo, M.; Nishimura, T.; Jona, H.; Honma, T.; Ito, S.; Morishima, *H. Tetrahedron* 1997, 53, 5937–5950.

We claim:

1. A compound of the general formula I:

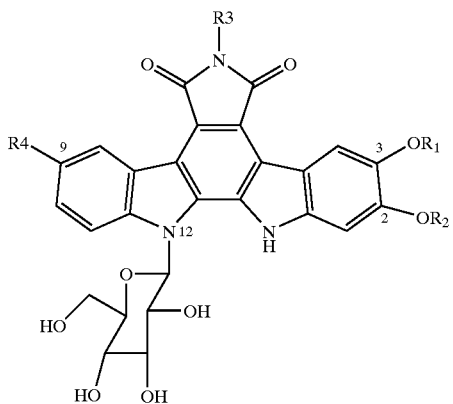

wherein $R_1$ and $R_2$ independently represent H, $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl, cyclo($C_{3-6}$) alkyl, aryl, or heterocycle, wherein aryl or heterocycle may each be unsubstituted or substituted with one or more of $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl or $R_1$ and $R_2$ combine to form a methylenedioxy, ethylenedioxy, propylenedioxy or a butylenedioxy group wherein one or more of the carbon atoms may be substituted with F, Cl, Br, I, $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl) amino, $C_{1-8}$ alkylamino-$C_{1-8}$ alkyl, di($C_{1-6}$ alkyl) amino-$C_{1-8}$ alkyl, cyclo($C_{3-6}$)alkyl, aryl or a heterocycle;

$R_3$ represents X, CO—X, $(CH_2)_{1-6}$-X, NHX, $NX_2$, $NH(CH_2)_{1-6}$-X, NHCOX, or $NHCO(CH_2)_{1-6}$-X wherein X represents H, OH, $NH_2$, CN, CHO, 2-hydroxy butyl, 3-sulfolane, 2-hydroxymethyl-3-hydroxypropyl, sulfonyl, mono- or polyfluorinated $C_{1-8}$ alkyl, ($C_{1-8}$)alkyl, $C_{1-8}$ alkoxy, cyclo($C_{3-6}$)alkyl, hydroxy($C_{1-6}$)alkyl, hydroxy($C_{1-6}$)alkoxy, dihydroxy ($C_{1-6}$)alkyl, aryloxy, aryl, heterocycle, gluconyl, mannonyl, gulonyl, glucuronyl, guluronyl, mannuronyl, or ethylmorpholinyl;

$R_4$ represents H, $NH_2$, $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl, cyclo($C_{3-6}$)alkyl, aryl or heterocycle; or a pharmaceutically acceptable salt thereof.

2. The compound of claim 1, wherein $R_1$ and $R_2$ combine to form a methylenedioxy ring, $R_3$ is H, and $R_4$ is OH.

3. The compound of claim 1, wherein $R_1$ and $R_2$ combine to form an ethylenedioxy ring, $R_3$ is H, and $R_4$ is OH.

4. The compound of claim 1, wherein $R_1$ and $R_2$ combine to form an isopropylenedioxy ring, $R_3$ is H, and $R_4$ is OH.

5. The compound of claim 1, wherein $R_1$ and $R_2$ are both $CH_3$, $R_3$ is H, and $R_4$ is OH.

6. The compound of claim 1, wherein $R_1$ and $R_2$ are both H, $R_3$ is H, and $R_4$ is OH.

7. A compound of the general formula II:

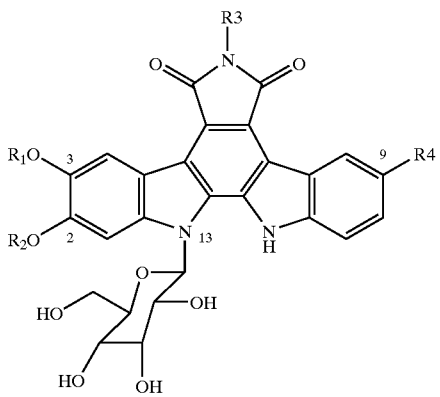

II wherein $R_1$ and $R_2$ independently represent H, $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl alkyl)amino-$C_{1-8}$ alkyl, cyclo($C_{3-6}$)alkyl, aryl, or heterocycle, wherein aryl or heterocycle may each be unsubstituted or substituted with one or more of $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl) amino-$C_{1-8}$ alkyl or $R_1$ and $R_2$ combine to form a methylenedioxy, ethylenedioxy, propylenedioxy or a butylenedioxy group wherein one or more of the carbon atoms may be substituted with F, Cl, Br, I, $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl, cyclo($C_{3-6}$)alkyl, aryl or a heterocycle;

$R_3$ represents X, CO—X, $(CH_2)_{1-6}$-X, NHX, $NX_2$, $NH(CH_2)_{1-6}$-X, NHCOX, or $NHCO(CH_2)_{1-6}$-X wherein X represents H, OH, $NH_2$, CN, CHO, 2-hydroxy butyl, 3-sulfolane, 2-hydroxymethyl-3-hydroxypropyl, sulfonyl, mono- or polyfluorinated $C_{1-8}$ alkyl, $(C_{1-8})$alkyl, $C_{1-8}$ alkoxy, cyclo($C_{3-6}$)alkyl, hydroxy($C_{1-6}$)alkyl, hydroxy($C_{1-6}$)alkoxy, dihydroxy $(C_{1-6})$alkyl, aryloxy, aryl, heterocycle, glyconyl, mannonyl, gulonyl, glycuronyl, guluronyl, mannuronyl, or (ethylmorpholinyl;

$R_4$ represents H, $NH_2$, $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl, cyclo($C_{3-6}$)alkyl, aryl or heterocycle; or a pharmaceutically acceptable salt thereof.

8. The compound of claim 7, wherein $R_1$ and $R_2$ combine to form a methylenedioxy ring, $R_3$ is H, and $R_4$ is OH.

9. The compound of claim 7, wherein $R_1$ and $R_2$ combine to form an ethylenedioxy ring, $R_3$ is H, and $R_4$ is OH.

10. The compound of claim 7, wherein $R_1$ and $R_2$ combine to form an isopropylenedioxy ring, $R_3$ is H, and $R_4$ is OH.

11. The compound of claim 7, wherein $R_1$ and $R_2$ are both $CH_3$, $R_3$ is H, and $R_4$ is OH.

12. The compound of claim 7, wherein $R_1$ and $R_2$ are both H, $R_3$ is H, and $R_4$ is OH.

13. A method of inhibiting topoisomerase I activity comprising administering to a mammal in need of inhibition of topoisomerase I activity an effective amount of at least one indolocarbazole analogue of the general formula I:

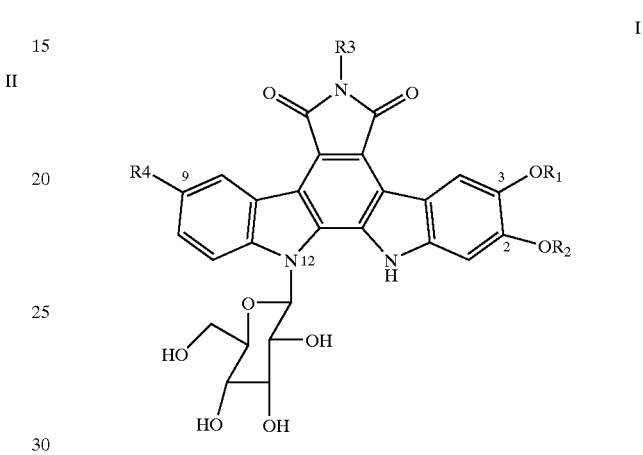

I wherein $R_1$ and $R_2$ independently represent H, $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl, cyclo($C_{3-6}$) alkyl, aryl, or heterocycle, wherein aryl or heterocycle may each be unsubstituted or substituted with one or more of $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl or $R_1$ and $R_2$ combine to form a methylenedioxy, ethylenedioxy, propylenedioxy or a butylenedioxy group wherein one or more of the carbon atoms may be substituted with F, Cl, Br, I, $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl) amino, $C_{1-8}$ alkylamino-$C_{1-8}$ alkyl, di($C_{1-6}$ alkyl) amino-$C_{1-8}$ alkyl, cyclo($C_{3-6}$)alkyl, aryl or a heterocycle;

$R_3$ represents X, CO—X, $(CH_2)_{1-6}$-X, NHX, $NX_2$, $NH(CH_2)_{1-6}$-X, NHCOX, or $NHCO(CH_2)_{1-6}$-X wherein X represents H, OH, $NH_2$, CN, CHO, 2-hydroxy butyl, 3-sulfolane, 2-hydroxymethyl-3-hydroxypropyl, sulfonyl, mono- or polyfluorinated $C_{1-8}$ alkyl, $(C_{1-8})$alkyl, $C_{1-8}$ alkoxy, cyclo($C_{3-6}$)alkyl, hydroxy($C_{1-6}$)alkyl, hydroxy($C_{1-6}$)alkoxy, dihydroxy $(C_{1-6})$alkyl, aryloxy, aryl, heterocycle, glyconyl, mannonyl, gulonyl, glycuronyl, guluronyl, mannuronyl, or ethylmorpholinyl;

$R_4$ represents H, $NH_2$, $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl, cyclo($C_{3-6}$)alkyl, aryl or heterocycle; or a pharmaceutically acceptable salt thereof. alone or in combination with a carrier.

14. The method of claim 13, wherein $R_1$ and $R_2$ combine to form a methylenedioxy ring, $R_3$ is H, and $R_4$ is OH.

15. The method of claim 13, wherein $R_1$ and $R_2$ combine to form an ethylenedioxy ring, $R_3$ is H, and $R_4$ is OH.

16. The method of claim 13, wherein $R_1$ and $R_2$ combine to form an isopropylenedioxy ring, $R_3$ is H, and $R_4$ is OH.

17. The method of claim 13, wherein $R_1$ and $R_2$ are both $CH_3$, $R_3$ is H, and $R_4$ is OH.

18. The method of claim 13, wherein $R_1$ and $R_2$ are both H, $R_3$ is H, and $R_4$ is OH.

19. A method of inhibiting topoisomerase I activity comprising administering to a mammal in need of inhibition of topoisomerase I activity an effective amount of at least one indolocarbazole analogue of the general formula II:

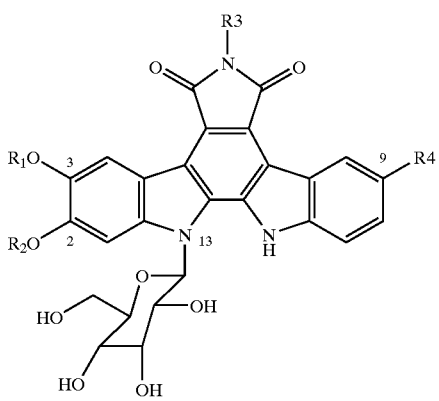

wherein
$R_1$ and $R_2$ independently represent H, $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl, cyclo($C_{3-6}$) alkyl, aryl, or heterocycle, wherein aryl or heterocycle may each be unsubstituted or substituted with one or more of $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl or $R_1$ and $R_2$ combine to form a methylenedioxy, ethylenedioxy, propylenedioxy or a butylenedioxy group wherein one or more of the carbon atoms may be substituted with F, Cl, Br, I, $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl) amino, $C_{1-8}$ alkylamino-$C_{1-8}$ alkyl, di($C_{1-6}$ alkyl) amino-$C_{1-8}$ alkyl, cyclo($C_{3-6}$)alkyl, aryl or a heterocycle;

$R_3$ represents X, CO—X, $(CH_2)_{1-6}$-X, NHX, or $NX_2$, $NH(CH_2)_{1-6}$-X, NHCOX, or $NHCO(CH_2)_{1-6}$-X wherein X represents H, OH, $NH_2$, CN, CHO, 2-hydroxy butyl, 3-sulfolane, 2-hydroxymethyl-3-hydroxypropyl, sulfonyl, mono- or polyfluorinated $C_{1-8}$ alkyl, ($C_{1-8}$)alkyl, $C_{1-8}$ alkoxy, cyclo($C_{3-6}$)alkyl, hydroxy($C_{1-6}$)alkyl, hydroxy($C_{1-6}$)alkoxy, dihydroxy ($C_{1-6}$)alkyl, aryloxy, aryl, heterocycle, glyconyl, mannonyl, gulonyl, glycuronyl, guluronyl, mannuronyl, or ethylmorpholinyl;

$R_4$ represents H, $NH_2$, $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl, cyclo($C_{3-6}$)alkyl, aryl or heterocycle; or
a pharmaceutically acceptable salt thereof, alone or in combination with a carrier.

20. The method of claim 19, wherein $R_1$ and $R_2$ combine to form a methylenedioxy ring, $R_3$ is H, and $R_4$ is OH.

21. The method of claim 19, wherein $R_1$ and $R_2$ combine to form an ethylenedioxy ring, $R_3$ is H, and $R_4$ is OH.

22. The method of claim 19, wherein $R_1$ and $R_2$ combine to form an isopropylenedioxy ring, $R_3$ is H, and $R_4$ is OH.

23. The method of claim 19, wherein $R_1$ and $R_2$ are both $CH_3$, $R_3$ is H, and $R_4$ is OH.

24. The method of claim 19, wherein $R_1$ and $R_2$ are both H, $R_3$ is H, and $R_4$ is OH.

25. A composition for inhibiting topoisomerase I activity comprising an effective amount of at least one compound of the general formula I:

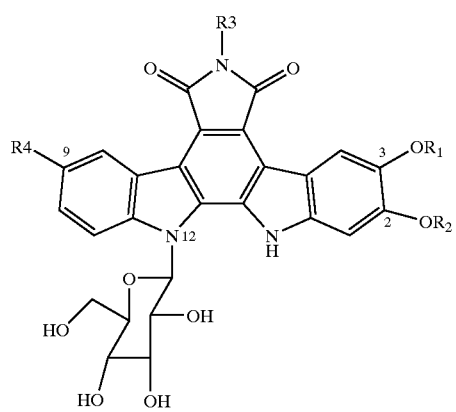

wherein
$R_1$ and $R_2$ independently represent H, $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl, cyclo($C_{3-6}$) alkyl, aryl, or heterocycle, wherein aryl or heterocycle may each be unsubstituted or substituted with one or more of $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl or $R_1$ and $R_2$ combine to form a methylenedioxy, ethylenedioxy, propylenedioxy or a butylenedioxy group wherein one or more of the carbon atoms may be substituted with F, Cl, Br, I, $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl) amino, C1-8 alkylamino-$C_{1-8}$ alkyl, di($C_{1-6}$ alkyl) amino-$C_{1-8}$ alkyl, cyclo($C_{3-6}$)alkyl, aryl or a heterocycle;

$R_3$ represents X, CO—X, $(CH_2)_{1-6}$-X, NHX, $NX_2$, $NH(CH_2)_{1-6}$-X, NHCOX, or $NHCO(CH_2)_{1-6}$-X wherein X represents H, OH, $NH_2$, CN, CHO, 2-hydroxy butyl, 3-sulfolane, 2-hydroxymethyl-3-hydroxypropyl, sulfonyl, mono- or polyfluorinated $C_{1-8}$ alkyl, ($C_{1-8}$)alkyl, $C_{1-8}$ alkoxy, cyclo($C_{3-6}$)alkyl, hydroxy($C_{1-6}$)alkyl, hydroxy($C_{1-6}$)alkoxy, dihydroxy ($C_{1-6}$)alkyl, aryloxy, aryl, heterocycle, glyconyl comprising gluconyl, mannonyl, gulonyl, glycuronyl comprising glucuronyl, guluronyl, mannuronyl, or ethylmorpholinyl;

$R_4$ represents H, $NH_2$, $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl, cyclo($C_{3-6}$)alkyl, aryl or heterocycle; or
a pharmaceutically acceptable salt thereof, in combination with a carrier or a pharmaceutical adjuvant or additive material.

26. The composition of claim 25, wherein $R_1$ and $R_2$ combine to form a methylenedioxy ring, $R_3$ is H, and $R_4$ is OH.

27. The composition of claim 25, wherein $R_1$ and $R_2$ combine to form an ethylenedioxy ring, $R_3$ is H, and $R_4$ is OH.

28. The composition of claim 25, wherein $R_1$ and $R_2$ combine to form an isopropylenedioxy ring, $R_3$ is H, and $R_4$ is OH.

29. The composition of claim 25, wherein $R_1$ and $R_2$ are both $CH_3$, $R_3$ is H, and $R_4$ is OH.

30. The composition of claim 25, wherein $R_1$ and $R_2$ are both H, $R_3$ is H, and $R_4$ is OH.

31. A composition for inhibiting topoisomerase I activity comprising an effective amount of at least one compound of the general formula II:

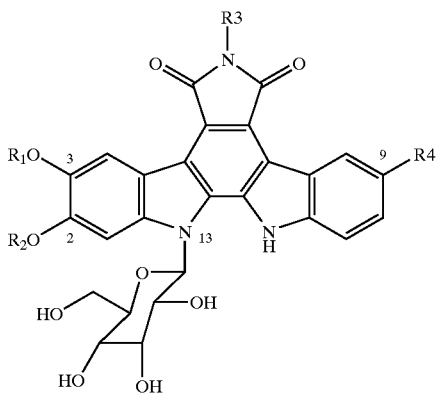

wherein $R_1$ and $R_2$ independently represent H, $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl, cyclo($C_{3-6}$) alkyl, aryl, or heterocycle, wherein aryl or heterocycle may each be unsubstituted or substituted with one or more of $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl or $R_1$ and $R_2$ combine to form a methylenedioxy, ethylenedioxy, propylenedioxy or a butylenedioxy group wherein one or more of the carbon atoms may be substituted with F, Cl, Br, I, $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl) amino, $C_{1-8}$ alkylamino-$C_{1-8}$ alkyl, di($C_{1-6}$ alkyl) amino-$C_{1-8}$ alkyl, cyclo($C_{3-6}$)alkyl, aryl or a heterocycle;

$R_3$ represents X, CO—X, $(CH_2)_{1-6}$-X, NHX, $NX_2$, $NH(CH_2)_{1-6}$-X, NHCOX, or $NHCO(CH_2)_{1-6}$-X wherein X represents H, OH, $NH_2$, CN, CHO, 2-hydroxy butyl, 3-sulfolane, 2-hydroxymethyl-3-hydroxypropyl, sulfonyl, mono- or polyfluorinated $C_{1-8}$ alkyl, $(C_{1-8})$alkyl, $C_{1-8}$ alkoxy, cyclo($C_{3-6}$)alkyl, hydroxy ($C_{1-6}$)alkyl, hydroxy ($C_{1-6}$)alkoxy, dihydroxy ($C_{1-6}$)alkyl, aryloxy, aryl, heterocycle, glyconyl mannonyl, gulonyl, glycuronyl guluronyl, mannuronyl, or ethylmorpholinyl;

$R_4$ represents H, $NH_2$, $C_{1-6}$ alkyl, aryl-$C_{1-6}$ alkyl, mono- or polyfluorinated $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, di($C_{1-6}$ alkyl)amino-$C_{1-8}$ alkyl, cyclo($C_{3-6}$)alkyl, aryl or heterocycle; or a pharmaceutically acceptable salt thereof, in combination with a carrier or a pharmaceutical adjuvant or additive material.

32. The composition of claim 31, wherein $R_1$ and $R_2$ combine to form a methylenedioxy ring, $R_3$ is H, and $R_4$ is OH.

33. The composition of claim 31, wherein $R_1$ and $R_2$ combine to form an ethylenedioxy ring, $R_3$ is H, and $R_4$ is OH.

34. The composition of claim 31, wherein $R_1$ and $R_2$ combine to form an isopropylenedioxy ring, $R_3$ is H, and $R_4$ is OH.

35. The composition of claim 31, wherein $R_1$ and $R_2$ are both $CH_3$, $R_3$ is H, and $R_4$ is OH.

36. The composition of claim 31, wherein $R_1$ and $R_2$ are both H, $R_3$ is H, and $R_4$ is OH.

37. A compound as in claims 1 or 7 wherein the aryl represents phenyl, naphthyl, phenanthracenyl or indanyl, each may be unsubstituted or substituted with one or more of OH, CN, $NO_2$, $NH_2$, $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, or di($C_{1-6}$ alkyl)amino-$C_{1-8}$ alkyl.

38. A compound as in claims 1 or 7 wherein the heterocycle represents piridyl, diazinyl, pyrimidinyl, pyrrolidinyl, piperazinyl, pyrrolyl, pyrazolyl, imidazolyl, imidazolidinyl, imidazolenyl, oxazolyl, isoxazolyl, thiazolyl, thiazolidinyl, thiazolinyl, isothiazolyl, isothiazolidinyl, isothiazolinyl, furanyl, thiophenyl, indolyl, benzthiopheneyl, benzofuranyl, 4-methyl 2,3 dihydro isocytosine, benzimidazolyl, benzothiozolyl, benzoxazolyl, benzisoxazolyl, 4-(2-hydroxyethyl)piperazine; 4-methyl 2,3 dihydro isocytosine, 1,4-dimethylpiperazine-2-formyl, piperidine, morpholine, isoindolyl, isobenzothiophenyl or isobenzofuranyl, 5-methoxy pyrimidinyl, (1,2,4)triazine-3,5-dione-6-yl, 6-mercaptopyrimidine-4yl, 4-methyl piperazinyl, pyranyl, 1-methyl pyrrol-2-yl, 2-methyl thiazol-4-yl, furan-2-yl, thiophen-2-yl, thiophen-3-yl or 3'-methoxy thiophen-3-yl, 4-(2-hydroxyethyl)piperazine, piperidine, 4-methyl 2,3 dihydro isocytosine, -(1H-1,2,4-triazol-1yl), 1,4-dimethylpiperazine, 4-methyl piperazinyl, morpholinyl, each may be unsubstituted or substituted with one or more of OH, CN, $NO_2$, $NH_2$, $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, or di($C_{1-6}$ alkyl)amino-$C_{1-8}$ alkyl.

39. A method as in claims 13 or 19 wherein the aryl represents phenyl, naphthyl, phenanthracenyl or indanyl, each may be unsubstituted or substituted with one or more of OH, CN, $NO_2$, $NH_2$, $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, or di($C_{1-6}$ alkyl)amino-$C_{1-8}$ alkyl.

40. A method as in claims 13 or 19 wherein the heterocycle represents piridyl, diazinyl, pyrimidinyl, pyrrolidinyl, piperazinyl, pyrrolyl, pyrazolyl, imidazolyl, imidazolidinyl, imidazolenyl, oxazolyl, isoxazolyl, thiazolyl, thiazolidinyl, thiazolinyl, isothiazolyl, isothiazolidinyl, isothiazolinyl, furanyl, thiophenyl, indolyl, benzthiopheneyl, benzofuranyl, 4-methyl 2,3 dihydro isocytosine, benzimidazolyl, benzothiozolyl, benzoxazolyl, benzisoxazolyl, 4-(2-hydroxyethyl)piperazine; 4-methyl 2,3 dihydro isocytosine, 1,4-dimethylpiperazine-2-formyl, piperidine, morpholine, isoindolyl, isobenzothiophenyl or isobenzofuranyl, 5-methoxy pyrimidinyl, (1,2,4)triazine-3,5-dione-6-yl, 6-mercaptopyrimidine-4yl, 4-methyl piperazinyl, pyranyl, 1-methyl pyrrol-2-yl, 2-methyl thiazol-4-yl, furan-2-yl, thiophen-2-yl, thiophen-3-yl or 3'-methoxy thiophen-3-yl, 4-(2-hydroxyethyl)piperazine, piperidine, 4-methyl 2,3 dihydro isocytosine, -(1H- 1,2,4-triazol-1yl), 1,4-dimethylpiperazine, 4-methyl piperazinyl, or morpholinyl, each may be unsubstituted or substituted with one or more of OH, CN, $NO_2$, $NH_2$, $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, or di($C_{1-6}$ alkyl)amino-$C_{1-8}$ alkyl.

41. A composition as in claims 25 or wherein the aryl represents phenyl, naphthyl, phenanthracenyl or indanyl, each may be unsubstituted or substituted with one or more of OH, CN, $NO_2$, $NH_2$, $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, or di($C_{1-6}$ alkyl)amino-$C_{1-8}$ alkyl.

42. A composition as in claims 25 or 31 wherein the heterocycle represents piridyl, diazinyl, pyrimidinyl, pyrrolidinyl, piperazinyl, pyrrolyl, pyrazolyl, imidazolyl, imidazolidinyl, imidazolenyl, oxazolyl, isoxazolyl, thiazolyl, thiazolidinyl, thiazolinyl, isothiazolyl, isothiazolidinyl, isothiazolinyl, furanyl, thiophenyl, indolyl, benzthiopheneyl, benzofuranyl, 4-methyl 2,3 dihydro isocytosine, benzimidazolyl, benzothiozolyl, benzoxazolyl, benzisoxazolyl, 4-(2-hydroxyethyl)piperazine; 4-methyl 2,3 dihydro isocytosine, 1,4-dimethylpiperazine-2-formyl, piperidine, morpholine, isoindolyl, isobenzothiophenyl or isobenzofuranyl, 5-methoxy pyrimidinyl, (1,2,4)triazine-3, 5-dione-6-yl, 6-mercaptopyrimidine-4yl, 4-methyl piperazinyl, pyranyl, 1-methyl pyrrol-2-yl, 2-methyl thiazol-4-yl, furan-2-yl, thiophen-2-yl, thiophen-3-yl or 3'-methoxy thiophen-3-yl, 4-(2-hydroxyethyl)piperazine, piperidine, 4-methyl 2,3 dihydro isocytosine, -(1H-1,2,4-triazol-1yl), 1,4-dimethylpiperazine, 4-methyl piperazinyl, or morpholinyl, each may be unsubstituted or substituted with one or more of OH, CN, $NO_2$, $NH_2$, $C_{1-6}$ alkyl, $C_{1-6}$ alkoxy, $C_{1-6}$ alkylamino, di($C_{1-6}$ alkyl)amino, $C_{1-8}$ alkylamino-$C_{1-8}$ alkyl, or di($C_{1-6}$ alkyl)amino-$C_{1-8}$ alkyl.

* * * * *

UNITED STATES PATENT AND TRADEMARK OFFICE
CERTIFICATE OF CORRECTION

| | |
|---|---|
| PATENT NO. | : 6,605,596 B2 |
| APPLICATION NO. | : 10/057260 |
| DATED | : August 12, 2003 |
| INVENTOR(S) | : David E. Zembower, Yongping Xie and Yasheen Zhou |

Page 1 of 2

It is certified that error appears in the above-identified patent and that said Letters Patent is hereby corrected as shown below:

At column 2, line 63, please delete "bycyclic" and insert therefor:
-- bicyclic --.

At column 3, line 23, please delete "bycyclic" and insert therefor:
-- bicyclic --.

At column 3, line 61, please delete "bycyclic" and insert therefor:
-- bicyclic --.

At column 4, line 8, please delete "piridyl" and insert therefor:
-- pyridyl --.

At column 4, line 14, please delete "bycyclic" and insert therefor:
-- bicyclic --.

At column 4, line 36, please delete "piridyl" and insert therefor:
-- pyridyl --.

At column 4, line 42, please delete "bycyclic" and insert therefor:
-- bicyclic --.

At column 30, line 43, please delete "hcterocycle" and insert therefor:
-- heterocycle --.

At column 30, line 66, please insert --OH,-- after "H" and before "$NH_2$"

At column 31, line 59, please delete "(ethylmorpholinyl;" and insert therefor:
-- ethylmorpholinyl; --.

At column 31, line 60, please insert --OH,-- after "H" and before "$NH_2$".

At column 32, line 59, please insert --OH,-- after "H" and before "$NH_2$".

At column 32, line 64, please delete "thereof." and insert therefor:
-- thereof --.

At column 33, line 59, please insert --OH,-- after "H" and before "$NH_2$".

At column 34, line 57, please insert --OH,-- after "H" and before "$NH_2$".

UNITED STATES PATENT AND TRADEMARK OFFICE
CERTIFICATE OF CORRECTION

PATENT NO. : 6,605,596 B2
APPLICATION NO. : 10/057260
DATED : August 12, 2003
INVENTOR(S) : David E. Zembower, Yongping Xie and Yasheen Zhou It is certified that error appears in the above-identified patent and that said Letters Patent is hereby corrected as shown below:

At column 35, line 60, please insert --OH,-- after "H" and before "$NH_2$"

At column 36, line 21, please delete "piridyl" and insert therefor:
-- pyridyl --.

At column 36, line 49, please delete "piridyl" and insert therefor:
-- pyridyl --.

At column 37, line 10, please delete "piridyl" and insert therefor:
-- pyridyl --.

Signed and Sealed this

Twenty-second Day of May, 2007

JON W. DUDAS
*Director of the United States Patent and Trademark Office*